US010519514B2

(12) United States Patent
Filer et al.

(10) Patent No.: US 10,519,514 B2
(45) Date of Patent: Dec. 31, 2019

(54) DETECTION METHOD FOR *NEISSERIA GONORRHOEAE*

(71) Applicant: Atlas Genetics Limited, Trowbridge, Wiltshire (GB)

(72) Inventors: Danny Filer, Bristol (GB); Claire Ferrao, Trowbridge (GB); Sharon Chadwick, Trowbridge (GB)

(73) Assignee: Atlas Genetics Limited, Trowbridge (GB)

( * ) Notice: Subject to any disclaimer, the term of this patent is extended or adjusted under 35 U.S.C. 154(b) by 1 day.

(21) Appl. No.: 15/511,893

(22) PCT Filed: Sep. 17, 2015

(86) PCT No.: PCT/GB2015/052693
§ 371 (c)(1),
(2) Date: Mar. 16, 2017

(87) PCT Pub. No.: WO2016/042333
PCT Pub. Date: Mar. 24, 2016

(65) Prior Publication Data
US 2017/0260572 A1 Sep. 14, 2017

(30) Foreign Application Priority Data

Sep. 17, 2014 (GB) .................................. 1416459.4

(51) Int. Cl.
C12Q 1/68 (2018.01)
C12Q 1/689 (2018.01)
(52) U.S. Cl.
CPC ....... *C12Q 1/689* (2013.01); *C12Q 2600/158* (2013.01); *C12Q 2600/16* (2013.01)
(58) Field of Classification Search
None
See application file for complete search history.

(56) References Cited

U.S. PATENT DOCUMENTS 5,541,308 A * 7/1996 Hogan ................. C21Q 1/6811
536/23.1
6,277,607 B1 * 8/2001 Tyagi ................... C12Q 1/6818
435/5

FOREIGN PATENT DOCUMENTS

WO 2002/079243 A2 10/2002
WO 2015/114368 A1 8/2015

OTHER PUBLICATIONS

NCBI Gene Database NGO1642, searched Nov. 6, 2018 (Year: 2018).*
Van Der Pol et al. (Journal of Clinical Microbiology vol. 44 Feb. 2006 p. 366) (Year: 2006).*
Vahidnia Ali et al: "Comparative evaluation of Roche Aurora FLOW, Becton and Dickinson Viper system, and Dynex DS2 for detection of Chlamydia trachomatis, Neisseria gonorrhoeae, and Trichomonas vaginalis in various clinical specimens", Diagnostic Microbiology and Infectious Disease, Nov. 2014, vol. 80, No. 3, Aug. 12, 2014, pp. 191-192.
Souza Elaine et al: "Label-free electrochemical detection of the specific oligonucleoide sequence of dengue virus type 1 on pencil graphite electrodes", Sensors (Basel, Switzerland) 2011, vol. 11, No. 6, pp. 5616-5629.
Fontenete Silvia et al: "Hybridization-based detection of Helicobacter pylori at human body temperature using advanced locked nucleic acid (LNA) probes", PLOS ONE, vol. 8, No. 11, E81230, Nov. 22, 2013, pp. 1-11.
Database ENA [Online], May 15, 2014, Lewis, L.A.: "Neissria gonorrhoeae Fa 1090, complete genome", XP002750693, retrieved from EBI, Database accession No. AE004969, abstract.
International Search Report issued in corresponding International Application No. PCT/GB2015/052693, dated Jan. 12, 2015, 5 pages.
Written Opinion of the International Searching Authority issued in corresponding International Application No. PCT/GB2015/052693, dated Jan. 12, 2015, 9 pages.

* cited by examiner

*Primary Examiner* — Katherine D Salmon
(74) *Attorney, Agent, or Firm* — Brown Rudnick LLP; Thomas C. Meyers

(57) ABSTRACT

A method of detecting the presence of *Neisseria gonorrhoeae* in a sample. The method involves detecting a first target sequence taken from the NGO1642 gene and/or a second target sequence taken from the NGO1012 gene. The method may involve a step of amplifying the target sequence, and may involve hybridising the target sequence to a nucleic acid probe and identifying hybridisation. The method may involve simultaneous detection of other target sequences, e.g. from other pathogens.

1 Claim, 21 Drawing Sheets
Specification includes a Sequence Listing.

NGT1F ▶
`AAGAACCCGC AACCGTCTGC AC`

```
1   aagaacccgc aaccgtctgc accgtaaatg taatcaactt caaacaaact gtccttccgg gcaacccgac catcctttaag
    ttcttgggcg tggcagacg attagttaac attagttgaa cagaaaggcc cgttgggctg gtagaaattc
```

NGT1 Probe ▶
`AACAAACT GTCTTTCCGG GCAACCCGAC C`

◀ NGT1R
`GAAA GCTGCACAGG CCCTTGAA`

```
81  ccagaacata ggtccgaaat aaaaaacttt cgacgtgtcc gggaactt
    ggtcctgtat ccgagcttta ttttttgaaa gctgcacagg cccttgaa
```

Fig. 3

```
  1  ATGTCTGTTG TCAATACGGC TGAAAATAGT TTTTTTCAGA TAGCGGCAGC CATACAACTC AAAGAGGAAG
     TACAGACAAC AGTTATGCCG ACTTTTATCA AAAAAAGTCT ATCGCCGTCG GTATGTTGAG TTTCTCCTTC

71  CAGAGTTTAT TGAGGATTCC GCACAATTTG CCCACATGTT GACCGATGCA CAACTGAATA CAAATGCACC
     GTCTCAAATA ACTCCTAAGG CGTGTTAAAC GGGTGTACAA CTGGCTACGT GTTGACTTAT GTTTACGTGG

141  GGGTGGTATT TTGTTGGTTT TAAAAGGTAG GGTTGGAGAT ACCGGTAAGC CGTTTTTATG TGTAATTAAG
     CCCACCATAA AACAACCAAA ATTTTCCATC CCAACCTCTA TGGCCATTCG GCAAAAATAC ACATTAATTC

211  GCTGAACCTC AAGATGGGTT CCGAACCAAA GAAGAGGATG ACTTTATCAC GATTGAATTC TTAGAAGAAT
     CGACTTGGAG TTCTACCCAA GGCTTGGTTT CTTCTCCTAC TGAAATAGTG CTAACTTAAG AATCTTCTTA

281  TATTACTGAC CGATTCAGCA AGATTATTCA AGATAGGTTT TTTGGTGGCT GAAACAGTAA GGCCGCTAGA
     ATAATGACTG GCTAAGTCGT TCTAATAAGT TCTATCCAAA AAACCACCGA CTTTGTCATT CCGGCGATCT

351  GCAAATACAA TCTGGGAATT ATCGAGCTTT TTTGTATGAC CATCTGATGA CACAAACGGA AACTAGACCG
     CGTTTATGTT AGACCCTTAA TAGCTCGAAA AAACATACTG GTAGACTACT GTGTTTGCCT TTGATCTGGC

421  GCAGCTTCCT ATTTCTATCA AGTATTCTTG GGTATGAGTA TAGCTGCTTC TTCCCGTAAA TTGACGCAGG
     CGTCGAAGGA TAAAGATAGT TCATAAGAAC CCATACTCAT ATCGACGAAG AAGGGCATTT AACTGCGTCC

491  ATTTTTTTGA GTGGACACGC AATTTTATCG ATAACTCTGA TTTAAGTGAT GATGCAAAAT TAGATGCGCA
     TAAAAAAACT CACCTGTGCG TTAAAATAGC TATTGAGACT AAATTCACTA CTACGTTTTA ATCTACGCGT

561  TGAAGCATTG CGCGTTACAT TGAAAAGTGC GGAAGCAACC ATTAGTGTAA ATAATTTTGC CCAAAATCAT
     ACTTCGTAAC GCGCAATGTA ACTTTTCACG CCTTCGTTGG TAATCACATT TATTAAAACG GGTTTTAGTA

631  TTACCTCAAG AAAAACGAAC AGCTTATACA GAATTTATGG TGGAAAAGGA TTTTCCTCAA AATGCCGTAA
     AATGGAGTTC TTTTTGCTTG TCGAATATGT CTTAAATACC ACCTTTTCCT AAAAGGAGTT TTACGGCATT
```

NG T2 Probe
                                                                [CGGTGTAGT]
                                          NG T2 Forward Primer >
                                          [ACGCAAACG][GAGGTCTTAC][GGATTTAG]
```
701  GTAAAGATAT TGAATATATT AAAACTCGTT TACGCAAACG GAGGTCTTAC GGATTTAGTA ACGGTGTAGT
     CATTTCTATA ACTTATATAA TTTTGAGCAA ATGCGTTTGC CTCCAGAATG CCTAAATCAT TGCCACATCA
```

< NG T2 Reverse Primer
                             [GTCCT][GATATACCTT][TAACGCGGTT][GC]
       NG T2 Probe >
       [TATCTTGACT][CCTCCCGAGC]
```
771  TATCTTGACT CCTCCCGAGC ATACTCAGGA CTATATGGAA ATTGCGCCAA CGGAAGATGG GGAATATACT
     ATAGAACTGA GGAGGGCTCG TATGAGTCCT GATATACCTT TAACGCGGTT GCCTTCTACC CCTTATATGA 841  GTTGTCCTAA TTAAAGGACA GTTACAACAA CAAAAATGA
     CAACAGGATT AATTTCCTGT CAATGTTGTT GTTTTTACT
```

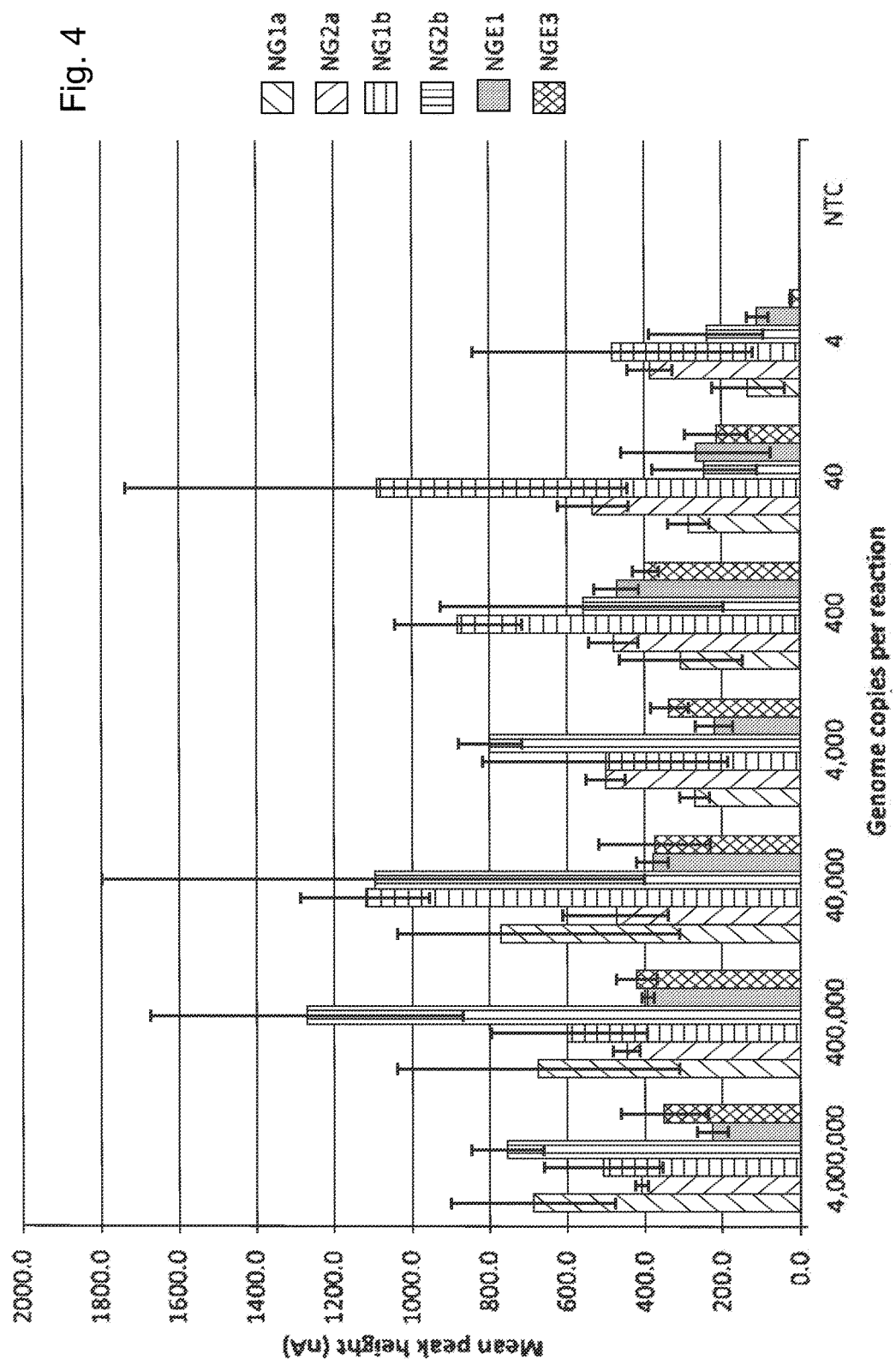

DETECTION METHOD FOR *NEISSERIA GONORRHOEAE*

CROSS-REFERENCE TO RELATED APPLICATIONS

This application is the U.S. national phase, pursuant to 35 U.S.C. § 371, of international application Ser. No. PCT/GB2015/052693, filed Sep. 17, 2015, designating the United States and published in English on Mar. 24, 2016 as publication No. WO 2016/042333 A1, which claims the benefit of Great Britain application number 1416459.4 filed Sep. 17, 2014, the disclosures of which are incorporated herein by reference in their entirety.

TECHNICAL FIELD

This invention is in the field of detection methods and primers, probes and compositions used in those methods. More specifically, the invention relates to methods of detecting *Neisseria gonorrhoeae* (*N. gonorrhoeae*) and primers, probes and compositions used in those methods and kits for performing the methods.

BACKGROUND ART

*N. gonorrhoeae* is a species of Gram-negative diplococci bacteria responsible for causing the sexually transmitted infection gonorrhoea.

Diagnosis of gonorrhea is usually achieved via a laboratory test including an overnight culture. The assay used to detect the presence of *N. gonorrhoeae* has a sensitivity range of 75-95%.

It is an object of the invention to provide a fast, reliable, sensitive and specific method of detecting *N. gonorrhoeae*.

DISCLOSURE OF THE INVENTION

The present invention is based on the identification of particular sequences that are present in the genomic DNA of *N. gonorrhoeae* and which allows for particularly effective detection of *N. gonorrhoeae*.

The inventors have identified two particular genes within the *N. gonorrhoeae* genome, NGO1642, which has been annotated as encoding a hypothetical, putative phage-associated protein and NGO1012, which has also been annotated as a phage associated protein. These annotations suggest that these genes were likely to have integrated into the *N. gonorrhoeae* genome at some point during the evolution of the *N. gonorrhoeae* chromosome either by transposition or via phage lysogeny. However, despite their putative function, the genes were not found to be present in other *Neisseria* species when tested in exclusivity trials and are well conserved in various strains of *N. gonorrhoeae* even when sourced from widely varying different geographical areas. This ability to distinguish *N. gonorrhoeae* from other *Neisseria* species is very useful in a detection method for *N. gonorrhoeae*.

The NGO1642 gene is particularly suitable for detection of the presence of *N. gonorrhoeae* in a sample because four copies of the gene are present in the *N. gonorrhoeae* genome and therefore it is easier to detect (because fewer rounds of amplification provide a large amount of amplified nucleic acid) than sequences present only once in the genome.

Two separate target sequences were identified because, due to the low population prevalence of 0.5% for *N. gonorrhoeae*, it is necessary to demonstrate a clinical specificity of 99.5% in order to achieve a positive predictive value (PPV) of greater than 90%. In order to achieve such a high level of specificity, the inventors identified two specific targets which when used together could provide the appropriate combined specificity.

Furthermore, the two sequences have been demonstrated by the inventors to be compatible with one another in terms of being amenable to simultaneous amplification and detection. Primers and probes have been designed which are capable of amplifying the two sequences simultaneously under the same conditions and subsequently detecting the two sequences simultaneously under the same conditions.

Accordingly, the invention provides a method of detecting the presence of *Neisseria gonorrhoeae* in a sample, comprising a step of detecting: a first target sequence of NGO1642 or a fragment thereof; and/or a second target sequence of NGO1012 or a fragment thereof.

The invention also provides a pair of primers that is capable of amplifying a sequence within NGO1642 to provide an amplicon in a polymerase chain reaction.

The invention also provides a forward primer comprising a nucleic acid sequence comprising 18 or more contiguous nucleotides selected from SEQ ID NO: 4, wherein the sequence of SEQ ID NO: 4 may be mutated by up to 5 additions, deletions and/or substitutions of single nucleotides.

The invention also provides a reverse primer comprising a nucleic acid sequence comprising 19 or more contiguous nucleotides selected from SEQ ID NO: 27 or SEQ ID NO: 5; wherein the sequence of SEQ ID NO: 27 or SEQ ID NO: 5 may be mutated by up to 5 additions, deletions and/or substitutions of single nucleotides.

The invention also provides a pair of primers that is capable of amplifying a sequence within NGO1012 to provide an amplicon in a polymerase chain reaction.

The invention also provides a forward primer comprising a nucleic acid sequence comprising 19 or more contiguous nucleotides selected from SEQ ID NO: 9 wherein the sequence of SEQ ID NO: 9 may be mutated by up to 5 additions, deletions and/or substitutions of single nucleotides.

The invention also provides a reverse primer comprising a nucleic acid sequence comprising 19 or more contiguous nucleotides selected from SEQ ID NO: 10; wherein the sequence of SEQ ID NO: 10 may be mutated by up to 5 additions, deletions and/or substitutions of single nucleotides.

The invention also provides a nucleic acid probe which is capable of hybridising to the NGO1642 sequence or a fragment thereof.

The invention also provides a nucleic acid probe comprising a nucleic acid sequence which comprises 19 or more contiguous nucleotides selected from a) SEQ ID NO: 26 or its complement; wherein the sequence of SEQ ID NO: 26 or its complement may be mutated by up to 5 additions, deletions and/or substitutions of single nucleotides; or b) SEQ ID NO: 3 or its complement; wherein the sequence of SEQ ID NO: 3 or its complement may be mutated by up to 5 additions, deletions and/or substitutions of single nucleotides.

The invention also provided a nucleic acid probe which is capable of hybridising to the NGO1012 sequence or a fragment thereof.

The invention also provides a nucleic acid probe comprising a nucleic acid sequence which comprises 20 or more contiguous nucleotides selected from SEQ ID NO: 8 or its complement; wherein the sequence of SEQ ID NO: 8 or its complement may be mutated by up to 5 additions, deletions and/or substitutions of single nucleotides.

The invention also provides a composition comprising a forward primer of the invention and a reverse primer of the invention.

The invention also provides a method of detecting the presence of Neisseria gonorrhoeae in a sample comprising a step of amplifying a first target sequence and a second target sequence and a step of detecting the first target sequence and the second target sequence, wherein the first target sequence consists of SEQ ID NO: 2 and the second target sequence consists of SEQ ID NO: 7, and said step of detecting comprises hybridising the first target sequence to a nucleic acid probe comprising SEQ ID NO: 3 and a ferrocene label, hybridising the second target sequence to a nucleic acid probe comprising SEQ ID NO: 8 and a ferrocene label, and identifying the occurrence of hybridisation by detecting the state of the labelled probes, and wherein said step of amplifying the first target sequence and the second target sequence uses the polymerase chain reaction and involves the use of forward primers consisting of SEQ ID NOs: 4 and 10 and reverse primers consisting of SEQ ID NOs: 5 and 11.

The invention also provides a method of detecting the presence of Neisseria gonorrhoeae in a sample comprising a step of amplifying a first target sequence and a second target sequence and a step of detecting the first target sequence and the second target sequence, wherein the first target sequence consists of SEQ ID NO: 25 and the second target sequence consists of SEQ ID NO: 7, and said step of detecting comprises hybridising the first target sequence to a nucleic acid probe comprising SEQ ID NO: 26 and a ferrocene label, hybridising the second target sequence to a nucleic acid probe comprising SEQ ID NO: 8 and a ferrocene label, and identifying the occurrence of hybridisation by detecting the state of the labelled probes, and wherein said step of amplifying the first target sequence and the second target sequence uses the polymerase chain reaction and involves the use of forward primers consisting of SEQ ID NOs: 4 and 10 and reverse primers consisting of SEQ ID NOs: 27 and 11.

The invention also provides a method of diagnosis of gonorrhoea comprising a method or using a primer, probe or composition of the invention.

The invention also provides a method for detecting N. gonorrhoeae, C. trachomatis and T. vaginalis in a sample.

Target Sequence(s)

The invention relates to methods, primers, probes, compositions and kits for detecting the presence of N. gonorrhoeae in a sample by the detection of a first target sequence and/or a second target sequence. The target sequences are nucleic acid sequences that are specific to N. gonorrhoeae, but should not be present in any species other than N. gonorrhoeae in order to reduce the occurrence of false positive results. The target sequences should be present in substantially all N. gonorrhoeae isolates irrespective of geographical origin in order to reduce the occurrence of false negative results. The target sequences are sequences that are particularly amenable to detection by rapid detection methods. The first target sequence and the second target sequence are such that they allow for multiplex detection, e.g. target sequences from other pathogens may be detected simultaneously with the first target sequence and/or the second target sequence of the invention.

The method for detecting the presence of N. gonorrhoeae in a sample may involve the detection of both the first target sequence and the second target sequence. The method may further involve the detection of other target sequences in addition to the first target sequence and/or the second target sequence. The method may involve the detection of at least one, at least two, at least three, at least four, at least five, at least six, at least seven, at least eight, at least nine or at least ten additional N. gonorrhoeae target sequences. The method for detecting the presence of N. gonorrhoeae in a sample may involve the detection of only one target sequence i.e., the first target sequence or the second target sequence.

The target sequence(s) may be any length which allows the target sequence to be identified as being specific to N. gonorrhoeae. In particular, the target sequence(s) may be 50-1000, 100-500, 200-400, 250-350, 200-300, 100-200 or 100-150 nucleotides in length.

The target sequence(s) that is detected may be DNA or RNA. Usually it is DNA, in particular genomic DNA.

The first target sequence is a target sequence of NGO1642. The second target sequence is a target sequence of NGO1012. The method for detecting the presence of N. gonorrhoeae in a sample may involve the detection of the first target sequence, or the second target sequence, or both the first target sequence and the second target sequence. The terms "first" and "second" are used merely for convenience, and the method may involve detecting the second target sequence irrespective of whether the method involves the detection of the first target sequence, and vice versa.

First Target Sequence

The method for detecting the presence of N. gonorrhoeae may comprise a step of detecting a first target sequence which is the NGO1642 sequence or a fragment thereof. In strain FA 1090, NGO1642 relates to nucleotides 1600891 to 1601214 of GI no. 59717368. Where the first target sequence is a fragment of NGO1642, the first target sequence may be any length within the NGO1642 sequence. For example, the first target sequence may be 50-350, 50-300, 100-250, 150-200, 50-100 or 50-150 nucleotides in length.

The first target sequence may be the NGO1642 sequence of SEQ ID NO: 1 or a fragment thereof, or its complement or a fragment thereof. As an alternative, the first target sequence may be any naturally occurring allele or variant of NGO1642 or a fragment thereof, or its complement or a fragment thereof. The first target sequence may be at least 90%, at least 95% or 100% identical to SEQ ID NO: 1 or at least 90%, at least 95% or 100% identical to a fragment of SEQ ID NO: 1 over the length of the fragment.

SEQ ID NO: 25 is a particular region within the NGO1642 sequence which has been found to be particularly useful as the first target sequence. The first target sequence may comprise 20-128 contiguous nucleotides of SEQ ID NO: 1 or its complement or SEQ ID NO: 25 or its complement. The first target sequence may comprise at least 22, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, or at least 125, contiguous nucleotides of SEQ ID NO: 1 or its complement or of SEQ ID NO: 25 or its complement. Preferably, the first target sequence to be detected comprises at least 23 contiguous nucleotides of SEQ ID NO: 1 or its complement. More preferably, the first target sequence to be detected comprises at least 18 contiguous nucleotides of SEQ ID NO: 25 or its complement.

SEQ ID NO: 2 is a particular region within the NGO1642 sequence which has been found to be particularly useful as the first target sequence. The first target sequence may comprise 20-140 contiguous nucleotides of SEQ ID NO: 1 or its complement or SEQ ID NO: 2 or its complement. The first target sequence may comprise at least 22, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, or at least 125, at least 130, at least 135 or at least 140 contiguous nucleotides of SEQ ID NO: 1 or its complement or of SEQ ID NO: 2 or its complement. Preferably, the first target sequence to be detected comprises at least 23 contiguous nucleotides of SEQ ID NO: 1 or its complement. More preferably, the first target sequence to be detected comprises at least 17 contiguous nucleotides of SEQ ID NO: 2 or its complement.

SEQ ID NOs 25 and 2 have overlapping sequences that are similar to one another. The sequence of SEQ ID NO: 25 lacks the 12 3' most nucleotides of SEQ ID NO: 2.

The first target sequence may comprise the nucleic acid sequence of SEQ ID NO: 1 or its complement, or SEQ ID NO: 25 or its complement, or SEQ ID NO: 2 or its complement. Alternatively, the first target sequence may consist of the nucleic acid sequence of SEQ ID NO: 1 or its complement, or SEQ ID NO: 25 or its complement, or SEQ ID NO: 2 or its complement.

The first target sequence may be DNA or RNA. Usually it is DNA, in particular genomic DNA.

Usually, the first target sequence will be part of a double stranded molecule.

Second Target Sequence

The method for detecting the presence of N. gonorrhoeae may comprise a step of detecting a second target sequence which is the NGO1012 sequence or a fragment thereof. In strain FA 1090, NGO1012 relates to nucleotides 979764 to 978886 of GI no. 59717368. Where a fragment is used, the second target sequence may be any length within the NGO1012 sequence. For example, the second target sequence may be 50-900, 100-500, 200-400, 250-350, 200-300, 100-200 or 100-150 nucleotides in length.

The second target sequence may be the NGO1012 sequence of SEQ ID NO: 6 or a fragment thereof, or its complement or a fragment thereof. As an alternative, the second target sequence may be any naturally occurring allele or variant of NGO1012 or a fragment thereof, or its complement or a fragment thereof. The second target sequence may be at least 90%, at least 95% or 100% identical to SEQ ID NO: 6 or at least 90%, at least 95% or 100% identical to a fragment of SEQ ID NO: 6 over the length of the fragment.

SEQ ID NO: 7 is a particular region within the NGO1012 sequence which has been found to be particularly useful as the second target sequence. The second target sequence may comprise 20-91 contiguous nucleotides of SEQ ID NO: 6 or its complement or SEQ ID NO: 7 or its complement. The second target sequence may comprise at least 22, at least 25, at least 30, at least 35, at least 40, at least 45, at least 50, at least 55, at least 60, at least 65, at least 70, at least 75, at least 80, at least 85 or at least 90 contiguous nucleotides of SEQ ID NO: 6 or its complement or of SEQ ID NO: 7 or its complement. Preferably, the second target sequence to be detected comprises at least 24 contiguous nucleotides of SEQ ID NO: 6 or its complement. More preferably, the second target sequence to be detected comprises at least 22 contiguous nucleotides of SEQ ID NO: 7 or its complement.

The second target sequence may comprise the nucleic acid sequence of SEQ ID NO: 6 or its complement, or SEQ ID NO: 7 or its complement. Alternatively, the second target sequence may consist of the nucleic acid sequence of SEQ ID NO: 6 or its complement, or SEQ ID NO: 7 or its complement.

The second target sequence may be DNA or RNA. Usually it is DNA, in particular genomic DNA.

Usually, the second target sequence will be part of a double stranded molecule.

Sample

The sample is a composition on which the method of the invention is performed in order to determine whether the target sequence(s) is present. The sample may be a composition in which the target sequence(s) is suspected to be present, or may be a composition in which the target sequence(s) is potentially present. Methods of detecting the presence of N. gonorrhoeae include methods that are performed on samples which are known or suspected to contain the target sequence(s), as well as compositions in which the target sequence(s) is only potentially present. Even if a method is performed on a composition in which the target sequence(s) is not actually present, the method is still considered to be a method of detecting the presence of N. gonorrhoeae if the method is performed to detect any N. gonorrhoeae that might be present. Similarly, the step of detecting relates to performing the step with the aim of detecting the target sequence(s), irrespective of whether it is present. Even if a step of detecting is performed on a composition in which the target sequence(s) is not actually present, the step is still considered to be a step of detecting if it is performed to detect any target sequence that might be present. For example identifying the occurrence of hybridisation (see below) refers to identifying the occurrence of any hybridisation which has occurred. Therefore, even if no hybridisation has occurred, the step is still considered to comprise identifying the occurrence of hybridisation if the step is performed to identify any occurrence of hybridisation that might have occurred.

The sample may be material obtained from a subject. The sample may be a cellular sample, i.e. a sample which contains human and/or bacterial cells. The sample may be obtained with minimal invasiveness or non-invasively, e.g., the sample may be a bodily fluid which may be obtained from a subject using a swab. Preferably, the sample is obtained from a genital swab, e.g. a vaginal swab. As an alternative, the sample may be a bodily fluid such as urine, ideally first catch urine.

The sample may have been treated since being obtained from the subject. For example, one skilled in the art will appreciate that samples can be purified, diluted, concentrated, centrifuged, frozen, etc. prior to target detection.

The subject is usually human, and may be male or female.

METHODS OF THE INVENTION

The methods of the invention for detecting the presence of N. gonorrhoeae involve detecting the presence of a first target sequence and/or a second target sequence using any technique. The methods involve a step of detecting the first target sequence and/or the second target sequence that is capable of specifically detecting the first target sequence and/or the second target sequence rather than any other nucleic acid sequence. The methods of the invention are thus sequence-specific. Preferably, the methods of the invention are rapid detection methods which allow for point-of-care diagnosis.

Usually, the method involves a step of amplifying the first target sequence and/or the second target sequence in addition to the step of detecting the first target sequence and/or the second target sequence. The method may be sequence-specific by virtue of a sequence-specific step of amplifying the first target sequence and/or the second target sequence.

Where a sequence-specific step of amplifying the first target sequence and/or the second target sequence is used, the step of detecting the first target sequence and/or the second target sequence does not need to be sequence-specific. As an alternative, the method may be sequence-specific by virtue of a sequence-specific step of detecting the first target sequence and/or the second target sequence. Where a sequence-specific step of detecting the first target sequence and/or the second target sequence is used, the step of amplifying the first target sequence and/or the second target sequence does not need to be sequence-specific. Usually, however, both the step of amplifying the first target sequence and/or the second target sequence and the step of detecting the first target sequence and/or the second target sequence are sequence-specific, as this can maximise overall specificity.

Therefore, the methods of the invention may involve a sequence-specific step of amplifying the first target sequence and/or the second target sequence and/or a sequence-specific step of detecting the first target sequence and/or the second target sequence.

Step of Amplifying

In typical embodiments, methods of the invention comprise a step of amplifying the first target sequence and/or the second target sequence. This is particularly the case if the detection step requires a large number of copies of the target sequence(s) to be present. As mentioned above, the step of amplifying the target sequence(s) is preferably sequence-specific.

The amplifying step may involve any method of nucleic acid amplification known in the art, including but not limited to the polymerase chain reaction (PCR), the ligase chain reaction (LCR)[1], strand displacement amplification (SDA)[2], transcription mediated amplification[3], nucleic acid sequence-based amplification (NASBA)[4], helicase-dependent amplification[5] and loop-mediated isothermal amplification[6]. Preferably, PCR is used.

A standard amplification mixture for PCR comprises: a forward primer and a reverse primer wherein the two primers are complementary to the 3' ends of the sense and antisense strand of the target sequence; a thermostable DNA polymerase; deoxynucleoside triphosphates (dNTPs); buffer; divalent cations (e.g. magnesium or manganese ions); and monovalent cations (e.g. potassium ions). The amplification mixture may comprise dUTPs instead of dTTPs and optionally uracil-DNA glycosylase, e.g. for use in decontamination methods. UTPs may be incorporated into the amplified sequences, allowing decontamination to be performed using uracil-DNA glycolase prior to subsequent amplifications. Using such methods, contaminating sequences from previous amplifications will contain uracil and may be removed without removing DNA sequences naturally present in the sample (which will not contain uracil).

A typical thermostable polymerase is a Taq polymerase from the thermophilic *bacterium Thermus aquaticus*. An alternative is Pfu polymerase from *Pyrococcus furiosus* which has a proof reading activity absent from Taq polymerase and is therefore a higher fidelity enzyme.

In some embodiments, the step of amplifying the first target sequence and/or the second target sequence involves the use of one or more of the primers of the invention, which are described in more detail below.

The step of amplifying the first target sequence and/or the second target sequence may be performed prior to or simultaneously with the step of detecting the first target sequence and/or the second target sequence. Amplification will typically take place before detection, with amplification and detection being distinct steps in an overall method.

Step of Detecting

As for the methods of detecting, As mentioned above, the step of detecting the first target sequence and/or the second target sequence will generally be sequence-specific. As an alternative, the step of detecting the first target sequence and/or the second target sequence may be non-sequence-specific, e.g. if the step of amplifying the first target sequence and/or the second target sequence is instead sequence-specific.

The detection step may involve hybridisation of the target sequence(s) to a nucleic acid probe and subsequent identification of hybridisation. Further details of such hybridisation techniques are described below. As an alternative, the step of detecting may involve sequencing of target sequence(s).

As mentioned above, in some embodiments, the step of detecting involves hybridising the first target sequence and/or the second target sequence to a nucleic acid probe. The nucleic acid probe may be any probe that is capable of specifically hybridising to the target sequence. Therefore, a probe used to hybridise to the first target sequence will generally comprise a fragment of SEQ ID NO: 1 (or its complement) or SEQ ID NO: 25 (or its complement) or SEQ ID NO: 2 (or its complement). A probe used to hybridise to the second target sequence will generally comprise a fragment of SEQ ID NO: 6 (or its complement) or SEQ ID NO: 7 (or its complement). Further details of nucleic acid probes are given below.

In some embodiments the detection step in a method of the invention involves identifying the occurrence of hybridisation after a probe has hybridised to a target sequence. Methods of identifying the occurrence of hybridisation include non-sequence-specific methods. Such methods include the use of a nucleic acid intercalating dye, for example, ethidium bromide or an asymmetrical cyanine dye, such as SYBR®-Green. These dyes increase their fluorescent signal when bound to double-stranded nucleic acid and may be detected by a standard fluorescence detection system.

Preferred methods of identifying the occurrence of hybridisation are sequence-specific methods, for example using a labelled nucleic acid probe. One or more labelled probes may be hybridised to the target sequence in a sequence-specific fashion. Nucleic acid probes may be labelled fluorescently, radioactively, enzymatically or electrochemically. Electrochemical labelling is preferred. The target sequence may be detected following hybridisation to an immobilised complementary sequence (for example, on a DNA array or "chip").

The step of detecting may include semi-specific detection of product. Such methods of identification include but are not limited to resolving the approximate molecular weight of the product, for example, by carrying out an electrophoresis of the reaction products prior to detection.

Some methods of identifying the occurrence of hybridisation involve detection of an intact hybridised probe, but others involve digestion or hydrolysis of the probe. Thus the nucleic acid probe may be degraded following hybridisation to the target sequence. This may be achieved using a double-strand specific exonuclease. This allows for detection of a label attached to the probe following hydrolysis of the probe, e.g. by changing the label's environment in such a way that may be detected in order to determine the presence or absence of the target sequence. This sort of detection is useful with electrochemically-active labels, as disclosed by Pearce et al.[7]. The exonuclease may be any 5' to 3' double strand specific exonuclease. The exonuclease may be selected from the group consisting of a *Thermus aquaticus* 5' to 3' exonuclease, a T7 exonuclease and a T5 exonuclease. Preferably, the exonuclease is a T7 exonuclease.

Identifying the occurrence of hybridisation may involve detecting the change in the environment of the label which occurs when the label is hydrolysed from the probe. With an electrochemical label, this change in environment of the probe may be detected by applying a potential difference to the sample and observing changes in the current flow.

Methods of identifying the occurrence of hybridisation may involve measurement of the hydrolysis of the probe concomitant with amplification of the target sequence. Such methods may make use of the nucleic acid exonuclease activity of a nucleic acid polymerase used in the step of amplifying the target sequence. Methods of amplification and detection using modified primers as described in international patent application PCT/GB2014/052213 (unpublished) may be used in the methods of the invention.

Amplification Primers

The invention also provides primers that are capable of specifically hybridising to the target sequences. The primers are capable of being extended using one of the nucleic acid amplification methods described above. The primers of the invention may be used in the methods of the invention, where a step of amplifying the target sequence(s) is used.

A primer of the invention will generally be at least 10 nucleotides long, e.g. the primer may be 12, 13, 14, 15, 16, 17, 18, 19, 20, 21, 22, 23, 24, 25, 26, 27, 28, 29, or 30 nucleotides in length. Shorter probe lengths are favoured if the GC content of the probe is high. The primer can be fully complementary to its target, but in some embodiments (e.g. in TMA) a primer can include a first region which is complementary to its target and a second region which is not.

Amplification of a target sequence will typically use two primers. These are usually referred to as "forward" and "reverse" primers, but the terms "forward" and "reverse" are used merely for convenience, and the directions specified in relation to each of the primer sequences are arbitrary. Therefore, primers described as forward may instead be reverse primers, and primers described as reverse may instead be forward primers. The primers of the invention are intended to be used in pairs, where the 3' ends of the two primers are directed towards one another so as to be useful in a step of amplifying.

The primers of the invention may comprise at least one modified nucleotide. The at least one modified nucleotide may protect the primer from exonuclease degradation. The presence of the at least one modified nucleotide in the primer may mean that the downstream amplified region cannot be hydrolysed by the exonuclease. Protection of the amplified product can be useful for increasing the signal produced during detection. Preferably, only one of the forward primer and the reverse primer comprises at least one modified nucleotide.

Modified Nucleotide

A modified nucleotide may be any nucleotide which comprises at least one modified sugar moiety, at least one modified internucleoside linkage and/or at least one modified nucleobase. The modification may prevent the nucleotide from being hydrolysed by an exonuclease. A modified nucleotide comprises at least one modification compared to a naturally occurring RNA or DNA nucleotide.

The at least one modified nucleotide may comprise at least one modified sugar moiety. The modified sugar moiety may be a 2'-O-methyl sugar moiety. The modified sugar moiety may be a 2'-O-methoxyethyl sugar moiety. The modified sugar may be a 2' fluoro modified sugar. As an alternative, the modified sugar moiety may be a bicyclic sugar. Bicyclic sugars include 4'-(CH$_2$)n-O-2' bridges, wherein n is 1 or 2; and 4'-CH(CH$_3$)—O-2' bridges.

The at least one modified nucleotide may comprise at least one modified internucleoside linkage.

The at least one modified internucleoside linkage may be at least one phosphoramidite linkage. The at least one modified internucleoside linkage may be at least one phosphorothioate linkage.

The at least one modified nucleotide may comprise at least one modified nucleobase.

The at least one modified nucleotide may comprise more than one modification, e.g. a modified nucleotide may comprise a modified sugar moiety and a modified internucleoside linkage. Alternatively, the modified nucleotide may comprise a modified sugar moiety and a modified nucleobase, or a modified internucleoside linkage and a modified nucleobase. The modified nucleotide may comprise a modified sugar moiety, a modified internucleoside linkage and a modified nucleobase.

The at least one modified nucleotide may be present at any position in the primer. For example the at least one modified nucleotide may be present at the 5' end of the primer, or may be present at the 3' end of the primer, or may be present in the central section of the primer, or may be interspersed throughout the primer. Usually, the at least one modified nucleotide is present at the 5' end of the primer. Where a modified nucleotide comprises a modified internucleoside linkage at the 5' end of the primer, this means that the internucleoside linkage between the first and second nucleotide is modified.

The modified primer may comprise multiple modified nucleotides. For example, the modified primer may comprise at least 2, at least 3, at least 4, at least 5, at least 6, at least 7, at least 8, at least 9 or at least 10 modified nucleotides. Specifically, the modified primer may comprise 1, 2, 3, 4, 5, 6, 7, 8, 9, 10, 11, 12, 13, 14, 15, 16, 17, 18, 19, 20, or more than 20 modified nucleotides. Each of the nucleotides of the modified primer may be modified nucleotides.

Where the modified primer comprises multiple modified nucleotides, the modified nucleotides are preferably contiguous nucleotides in the primer. As an alternative, the modified nucleotides may be spaced out along the primer, i.e. one or more unmodified nucleotides may be present in between the modified nucleotides. The spaces of unmodified nucleotides may comprise, 1, 2, 3, 4, 5, 6, 7, 8, 9 or 10 or more unmodified nucleotides.

Preferably, the primer comprises 3 or 4 modified nucleotides ideally contiguous. These may be at the 5' end. Preferably, the 3 or 4 modified nucleotides comprise phosphorothioate linkages. In some embodiments, the primer comprises 3 contiguous phosphorothioate linkages at the 5' end, i.e. the linkages between each of the first to fourth nucleotides are phosphorothioate linkages. In some embodiments, the primer comprises four contiguous phosphorothioate linkages at the 5' end, i.e. the linkages between each of the first to fifth nucleotides are phosphorothioate linkages.

Amplification Primers Capable of Specifically Hybridising to the First Target Sequence A forward primer of the invention may comprise any nucleic acid sequence capable of specifically hybridising to SEQ ID NO: 1 or its complement SEQ ID NO: 25 or its complement or SEQ ID NO: 2 or its complement.

A forward primer of the invention may comprise a nucleic acid sequence comprising at least 10 contiguous nucleotides of SEQ ID NO: 4. This sequence may be mutated by up to 5 additions, deletions and/or substitutions of single nucleotides relative to SEQ ID NO: 4, provided that the primer is still capable of specifically hybridising to the first target sequence. In some embodiments there are 1, 2, 3, 4 or 5 additions, deletions and/or substitutions of single nucleotides relative to SEQ ID NO: 4. However, in other embodiments there are no additions, deletions and/or substitutions of single nucleotides made to SEQ ID NO: 4. Preferably, the forward primer comprises a nucleic acid sequence comprising at least 11, at least 12, at least 13, at least 14, at least 15, at least 16, at least 17, at least 18, at least 19, at least 20 or at least 21 contiguous nucleotides of SEQ ID NO: 4. Even more preferably, the forward primer comprises all of the nucleic acid sequence of SEQ ID NO: 4. The forward primer may consist of the nucleic acid sequence of SEQ ID NO: 4.

In one embodiment, the forward primer may comprise or consist of the nucleotide sequence of A*A*G*A*ACCCGCAACCGTCTGCAC (SEQ ID NO: 4) or A*A*G*AACCCGCAACCGTCTGCAC.

N* indicates that the nucleotide at the specified position is a modified nucleotide. Where the modified nucleotide N*comprises a modified internucleoside linkage the modified internucleoside linkage is between the specified nucleotide and the next nucleotide in the 3' direction.

Therefore, the forward primer may comprise the nucleotide sequence of SEQ ID NO: 4, wherein nucleotides 1-3 or 1-4 are modified nucleotides. The nucleotides of the primer are numbered from the 5' end. Therefore nucleotides 1-3 or 1-4 are the 3 or 4 nucleotides at the 5' end of the primer. The modified nucleotides may comprise phosphorothioate linkages.

A reverse primer of the invention may comprise any nucleic acid sequence capable of specifically hybridising to SEQ ID NO: 1 or its complement, SEQ ID NO: 25 or its complement, or SEQ ID NO: 2 or its complement. A reverse primer of the invention may be used in combination with a forward primer of the invention that is capable of specifically hybridising to SEQ ID NO: 1 or its complement, SEQ ID NO: 25 or its complement, or SEQ ID NO: 2 or its complement, to amplify the first target sequence. Preferably, the reverse primer of the invention is capable of hybridising to the strand of the first target sequence that is complementary to the strand of the first target sequence to which the forward primer of the invention hybridises.

The reverse primer may comprise a nucleic acid sequence comprising at least 10 contiguous nucleotides of SEQ ID NO: 27. This sequence may be mutated by up to 5 additions, deletions and/or substitutions of single nucleotides relative to SEQ ID NO: 27. In some embodiments there are 1, 2, 3, 4 or 5 additions, deletions and/or substitutions of single nucleotides relative to SEQ ID NO: 27. However, in other embodiments there are no additions, deletions and/or substitutions of single nucleotides made to SEQ ID NO: 27. Preferably, the reverse primer comprises a nucleic acid sequence comprising at least 11, at least 12, at least 13, at least 14, at least 15, at least 16, at least 17, at least 18, at least 19, at least 20, at least 21 or at least 22 contiguous nucleotides of SEQ ID NO: 27. Even more preferably, the reverse primer comprises all of the nucleic acid sequence of SEQ ID NO: 27. The reverse primer may consist of the nucleic acid sequence of SEQ ID NO: 27.

The reverse primer may comprise or consist of the nucleotide sequence of A*A*G*T*TCCCGGACACGTCGAAAG (SEQ ID NO: 27) or A*A*G*TTCCCGGACACGTCGAAAG, i.e. the first primer may comprise the nucleotide sequence of SEQ ID NO: 27, wherein nucleotides 1-3 or 1-4 are modified nucleotides. The modified nucleotides may comprise phosphorothioate linkages.

The reverse primer may comprise a nucleic acid sequence comprising at least 10 contiguous nucleotides of SEQ ID NO: 5. This sequence may be mutated by up to 5 additions, deletions and/or substitutions of single nucleotides relative to SEQ ID NO: 5. In some embodiments there are 1, 2, 3, 4 or 5 additions, deletions and/or substitutions of single nucleotides relative to SEQ ID NO: 5. However, in other embodiments there are no additions, deletions and/or substitutions of single nucleotides made to SEQ ID NO: 5. Preferably, the reverse primer comprises a nucleic acid sequence comprising at least 11, at least 12, at least 13, at least 14, at least 15, at least 16, at least 17, at least 18, at least 19, at least 20, at least 21, at least 22, at least 23, at least 24 or at least 25 contiguous nucleotides of SEQ ID NO: 5. Even more preferably, the reverse primer comprises all of the nucleic acid sequence of SEQ ID NO: 5. The reverse primer may consist of the nucleic acid sequence of SEQ ID NO: 5.

The reverse primer may comprise or consist of the nucleotide sequence of C*T*C*C*GTCTCCATAAGTTCCCGGACAC (SEQ ID NO: 5) or C*T*C*CGTCTCCATAAGTTCCCGGACAC, i.e. the first primer may comprise the nucleotide sequence of SEQ ID NO: 5, wherein nucleotides 1-3 or 1-4 are modified nucleotides. The modified nucleotides may comprise phosphorothioate linkages.

The invention provides a pair of primers that is capable of amplifying a first target sequence within NGO1642 to provide an amplicon. Primer pairs of the invention of particular interest are those useful in PCR, and one such pair is embodied as SEQ ID NOs: 4 and 5. Another such pair is embodied as SEQ ID NOs: 4 and 27. The invention also provides pairs of primers comprising a primer comprising SEQ ID NO: 4, wherein nucleotides 1-3 or 1-4 are modified nucleotides optionally comprising phosphorothioate linkages, and a primer comprising SEQ ID NO: 27, wherein SEQ ID NO: 27 is unmodified, i.e. comprises no modified nucleotides. The invention also provides pairs of primers comprising a primer comprising SEQ ID NO: 27, wherein nucleotides 1-3 or 1-4 are modified nucleotides optionally comprising phosphorothioate linkages, and a primer comprising SEQ ID NO: 4, wherein SEQ ID NO: 4 is unmodified, i.e. comprises no modified nucleotides.

The invention also provides pairs of primers comprising a primer comprising SEQ ID NO: 4, wherein nucleotides 1-3 or 1-4 are modified nucleotides optionally comprising phosphorothioate linkages, and a primer comprising SEQ ID NO: 5, wherein SEQ ID NO: 5 is unmodified, i.e. comprises no modified nucleotides. The invention also provides pairs of primers comprising a primer comprising SEQ ID NO: 5, wherein nucleotides 1-3 or 1-4 are modified nucleotides optionally comprising phosphorothioate linkages, and a primer comprising SEQ ID NO: 4, wherein SEQ ID NO: 4 is unmodified, i.e. comprises no modified nucleotides.

Amplification Primers Capable of Specifically Hybridising to the Second Target Sequence A forward primer of the invention may comprise any nucleic acid sequence capable of specifically hybridising to SEQ ID NO: 6 or its complement or SEQ ID NO: 7 or its complement.

A forward primer of the invention may comprise a nucleic acid sequence comprising at least 10 contiguous nucleotides of SEQ ID NO: 9. This sequence may be mutated by up to 5 additions, deletions and/or substitutions of single nucleotides relative to SEQ ID NO: 9, provided that the primer is still capable of specifically hybridising to the second target sequence. In some embodiments there are 1, 2, 3, 4 or 5 additions, deletions and/or substitutions of single nucleotides relative to SEQ ID NO: 9. However, in other embodiments there are no additions, deletions and/or substitutions of single nucleotides made to SEQ ID NO: 9. Preferably, the forward primer comprises a nucleic acid sequence comprising at least 11, at least 12, at least 13, at least 14, at least 15, at least 16, at least 17, at least 18, at least 19, at least 20, at least 21, at least 22, at least 23, at least 24, at least 25 or at least 26 contiguous nucleotides of SEQ ID NO: 9. Even more preferably, the forward primer comprises all of the nucleic acid sequence of SEQ ID NO: 9. The forward primer may consist of the nucleic acid sequence of SEQ ID NO: 9.

In one embodiment, the forward primer may comprise or consist of the nucleotide sequence of A*C*G*C*AAACGGAGGTCTTACGGATTTAG (SEQ ID NO: 9) or A*C*G*CAAACGGAGGTCTTACGGATTTAG.

N* indicates that the nucleotide at the specified position is a modified nucleotide. Where the modified nucleotide N*comprises a modified internucleoside linkage the modified internucleoside linkage is between the specified nucleotide and the next nucleotide in the 3' direction.

Therefore, the forward primer may comprise the nucleotide sequence of SEQ ID NO: 9, wherein nucleotides 1-3 or 1-4 are modified nucleotides. The nucleotides of the primer are numbered from the 5' end. Therefore nucleotides 1-3 or 1-4 are the 3 or 4 nucleotides at the 5' end of the primer. The modified nucleotides may comprise phosphorothioate linkages.

A reverse primer of the invention may comprise any nucleic acid sequence capable of specifically hybridising to SEQ ID NO: 6 or its complement, or SEQ ID NO: 7 or its complement. A reverse primer of the invention may be used in combination with a forward primer of the invention that is capable of specifically hybridising to SEQ ID NO: 6 or its complement, or SEQ ID NO: 7 or its complement, to amplify the second target sequence. Preferably, the reverse primer of the invention is capable of hybridising to the strand of the second target sequence that is complementary to the strand of the second target sequence to which the forward primer of the invention hybridises.

The reverse primer may comprise a nucleic acid sequence comprising at least 10 contiguous nucleotides of SEQ ID NO: 10. This sequence may be mutated by up to 5 additions, deletions and/or substitutions of single nucleotides relative to SEQ ID NO: 10. In some embodiments there are 1, 2, 3, 4 or 5 additions, deletions and/or substitutions of single nucleotides relative to SEQ ID NO: 10. However, in other embodiments there are no additions, deletions and/or substitutions of single nucleotides made to SEQ ID NO: 10. Preferably, the reverse primer comprises a nucleic acid sequence comprising at least 11, at least 12, at least 13, at least 14, at least 15, at least 16, at least 17, at least 18, at least 19, at least 20, at least 21, at least 22, at least 23, at least 24, at least 25 or at least 26 contiguous nucleotides of SEQ ID NO: 10. Even more preferably, the reverse primer comprises all of the nucleic acid sequence of SEQ ID NO: 10. The reverse primer may consist of the nucleic acid sequence of SEQ ID NO: 10.

The reverse primer may comprise or consist of the nucleotide sequence of C*G*T*T*GGCGCAATTTCCATATAGTCCTG (SEQ ID NO: 10) or C*G*T*TGGCGCAATTTCCATATAGTCCTG, i.e. the first primer may comprise the nucleotide sequence of SEQ ID NO: 10, wherein nucleotides 1-3 or 1-4 are modified nucleotides. The modified nucleotides may comprise phosphorothioate linkages.

The invention provides a pair of primers that is capable of amplifying a first target sequence within NGO1012 to provide an amplicon. Primer pairs of the invention of particular interest are those useful in PCR, and one such pair is embodied as SEQ ID NOs: 10 and 11. The invention also provides pairs of primers comprising a primer comprising SEQ ID NO: 9, wherein nucleotides 1-3 or 1-4 are modified nucleotides optionally comprising phosphorothioate linkages, and a primer comprising SEQ ID NO: 10, wherein SEQ ID NO: 10 is unmodified, i.e. comprises no modified nucleotides. The invention also provides pairs of primers comprising a primer comprising SEQ ID NO: 10, wherein nucleotides 1-3 or 1-4 are modified nucleotides optionally comprising phosphorothioate linkages, and a primer comprising SEQ ID NO: 9, wherein SEQ ID NO: 9 is unmodified, i.e. comprises no modified nucleotides.

Nucleic Acid Probes

The invention provides nucleic acid probes that are capable of specifically hybridising to a target sequence. The nucleic acid probes may be used in the step of detecting the first target sequence and/or the second target sequence in the methods of the invention. The probes are normally labelled.

Nucleic acid probes of the invention are typically 15 to 45 nucleotides in length, i.e. the nucleic acid probe may be 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 nucleotides in length.

As mentioned above, a probe capable of specifically hybridising to the first target sequence will generally comprise a fragment of SEQ ID NO: 1 or its complement or a fragment of SEQ ID NO: 25 or its complement or a fragment of SEQ ID NO: 2 or its complement. One such fragment is SEQ ID NO: 3. Another such fragment is SEQ ID NO: 26. The nucleic acid probe may comprise a sequence comprising at least 19, at least 20 or at least 21 contiguous nucleotides from SEQ ID NO: 26 or its complement; wherein the sequence may be mutated by up to 5 additions, deletions and/or substitutions of single nucleotides relative to SEQ ID NO: 26 or its complement, provided that the sequence is still capable of specifically hybridising to the first target sequence and that the occurrence of the hybridisation may be identified. In some embodiments there are 1, 2, 3, 4 or 5 additions, deletions and/or substitutions of single nucleotides relative to SEQ ID NO: 26 or its complement. However, in other embodiments there are no additions, deletions or substitutions relative to SEQ ID NO: 26 or its complement. The nucleic acid probe may comprise a sequence comprising at least 19, at least 20 or at least 21 contiguous nucleotides from SEQ ID NO: 3 or its complement; wherein the sequence may be mutated by up to 5 additions, deletions and/or substitutions of single nucleotides relative to SEQ ID NO: 3 or its complement, provided that the sequence is still capable of specifically hybridising to the first target sequence and that the occurrence of the hybridisation may be identified. In some embodiments there are 1, 2, 3, 4 or 5 additions, deletions and/or substitutions of single nucleotides relative to SEQ ID NO: 3 or its complement. However, in other embodiments there are no additions, deletions or substitutions relative to SEQ ID NO: 3 or its complement.

A probe capable of specifically hybridising to the second target sequence will generally comprise a fragment of SEQ ID NO: 6 or its complement or a fragment of SEQ ID NO: 7 or its complement. One such fragment is SEQ ID NO: 8. The nucleic acid probe may comprise a sequence comprising at least 20, at least 21, at least 22, at least 23, at least 24, at least 25, at least 26, at least 27 or at least 29 contiguous nucleotides from SEQ ID NO: 8 or its complement; wherein the sequence may be mutated by up to 5 additions, deletions and/or substitutions of single nucleotides relative to SEQ ID NO: 8 or its complement, provided that the sequence is still capable of specifically hybridising to the second target sequence and that the occurrence of the hybridisation may be identified. In some embodiments there are 1, 2, 3, 4 or 5 additions, deletions and/or substitutions of single nucleotides relative to SEQ ID NO: 8 or its complement. However, in other embodiments there are no additions, deletions or substitutions relative to SEQ ID NO: 8 or its complement.

The nucleic acid probes may include one or more additional moieties other than the region capable of hybridising to the target sequence. The additional moieties may be additional nucleic acid sequences or be non-nucleic acid moieties. For example, the probe may include a linker region which attaches it to an array. The additional moiety may be a label moiety. Particular types of labels that may be used are described in more detail below.

Labels

The nucleic acid probes and/or primers described above may be linked to a label to assist their detection. That label may be radioactive, enzymatically active, fluorescently active, luminescently active, or electrochemically active.

Where detection of multiple nucleic acid sequences are undertaken simultaneously, for example where the first target sequence and the second target sequence are both detected; or where detection of the first target sequence and/or the second target sequence and detection of an internal control nucleic acid sequence are both undertaken simultaneously; or where detection of the first target sequence and/or the second target sequence and detection of one or more additional target sequences are undertaken simultaneously, the labels used to assist in the detection of the multiple nucleic acid sequences are preferably distinguishable from each other. For example, they may be different fluorophores or they may be different electrochemically active agents or electrochemically active labels providing electrochemically distinguishable activity.

The present invention is especially suitable for use with electrochemically labelled probes. In particular, the electrochemical label may include those comprising metallo-carbocyclic pi complexes, that is organic complexes with partially or fully delocalized pi electrons. Suitable labels include those comprising sandwich compounds in which two carbocyclic rings are parallel, and also bent sandwiches (angular compounds) and monocyclopentadienyls. Preferably, the electrochemically active markers are metallocene labels. More preferably they are ferrocene labels. These can be used as disclosed by Pearce et al.[7] Examples of labels which may be used in the methods of the invention can be found in WO03/074731, WO2012/085591 and WO 2013/190328. For example, the ferrocene label may have the structure of formula I in WO2012/085591. As an alternative, the ferrocene label may have the structure of formula I in WO 2013/190328.

Internal Control

Methods of the invention will generally include an internal control nucleic acid. This is used to provide confirmation that the step of amplifying the first target sequence and/or the second target sequence and/or the step of detecting the first target sequence and/or the second target sequence works correctly.

The internal control comprises a nucleic acid sequence that will not be present in the sample. The internal control nucleic acid sequence may be taken from a plant or *bacterium*, wherein the nucleic acid sequence is not present in animals and is highly specific to this plant or *bacterium*. One example of a possible *bacterium* from which the control nucleic acid may be taken for an animal sample is *Pectobacterium atrosepticum*, although any control nucleic acid may be used that will not be present in the sample.

The internal control nucleic acid sequence may be DNA or RNA, but is preferably DNA.

The techniques described above for detecting and amplifying the first target sequence and/or the second target sequence can also be used for detection and amplification of an internal control nucleic acid sequence. Similarly, the characteristics of primers and probes can be the same as described above.

Thus the internal control nucleic acid may be any length provided that it is capable of being identified as the internal control nucleic acid. For example, the internal control nucleic acid may be 50-1000, 100-500, 100-200 or 100-150 nucleotides in length. In particular, the internal control nucleic acid sequence may be 50, 100, 105, 110, 120, 130, 140, 150, 200, 250, 300, 350, 400, 450, 500, 550, 600, 650, 700, 750, 800, 850, 900, 950 or 1000 nucleotides in length. Ideally, the length of the internal control nucleic acid is similar to the length of the target sequence.

The internal control nucleic acid may comprise the nucleic acid sequence of SEQ ID NO: 11, or its complement, or a fragment of SEQ ID NO: 11 or its complement; wherein the sequence is mutated by up to 5 additions, deletions or substitutions of single nucleotides. The internal control nucleic acid sequence may be mutated by up to 5 additions, deletions and/or substitutions of single nucleotides relative to SEQ ID NO: 11 or its complement.

The step of detecting the internal control nucleic acid sequence is ideally conducted using the same technique(s) as that used to detect the first target sequence and/or the second target sequence.

Where the step of detecting the internal control nucleic acid sequence involves hybridisation of the internal control nucleic acid sequence to a nucleic acid probe, the nucleic acid probe may comprise a nucleic acid sequence comprising at least 20 contiguous nucleotides containing SEQ ID NO: 12 or its complement; wherein the sequence may be mutated by up to 5 additions, deletions and/or substitutions of single nucleotides relative to SEQ ID NO: 12 provided that the sequence is still capable of specifically hybridising to the internal control nucleic acid sequence. In some embodiments there are 1, 2, 3, 4 or 5 additions, deletions and/or substitutions of single nucleotides relative to SEQ ID NO: 12. However, in other embodiments there are no additions, deletions and/or substitutions of single nucleotides made to SEQ ID NO: 12.

Where used, a step of amplifying the internal control nucleic acid sequence may involve the same technique(s) as the step of amplifying the first target sequence and/or the second target sequence, or may involve different techniques than the step of amplifying the first target sequence and/or the second target sequence. Preferably, the step of amplifying the internal control nucleic acid sequence is conducted using the same technique as that used to amplify the first target sequence and/or the second target sequence.

Where the internal control nucleic acid sequence is that of SEQ ID NO: 11, a forward control primer having the sequence of SEQ ID NO: 13 and a reverse control primer having a sequence of SEQ ID NO: 14 may be used as the primer pair used in a step of amplifying the internal control nucleic acid sequence. The forward and reverse control primers may, however, be longer or shorter in length than SEQ ID NOs: 14 and 15, respectively. The forward and reverse control primers may be 12 to 60 nucleotides in length, i.e. the primers may be 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 nucleotides in length. Shorter probe lengths are favoured if the GC content of the probe is high.

Use of Shorter Primers and Probes

In some embodiments, primers and probes may be shorter than those specified above particularly if steps are taken to increase the annealing temperature of the primer. In particular, lengths of 1, 2, 3, 4 or 5 nucleotide residues shorter than the lengths and ranges specifically disclosed above are contemplated.

The use of shorter primer and probes may be facilitated by the use of minor groove binder moieties and also locked nucleic acids (LNAs) which increase thermal stability of primers and probes and increase the annealing temperature of the primer or probe. The use of such modifications is contemplated as part of the present invention in conjunction with probes and primers as disclosed above, but with oligomeric lengths and ranges shortened by 5 residues from those specified above. The present invention contemplates use of shorter primer and probes wherein increased thermal stability is facilitated by the use of minor groove binder moieties and/or LNAs in combination with primers and probes described herein which do not have increased thermal stability as facilitated by the use of minor groove binder moieties and/or LNAs as well as exclusive use of primers and probes having increased thermal stability as facilitated by the use of minor groove binder moieties and/or lock nucleic acids.

Locked Nucleic Acids

Locked nucleic acids (LNAs) are well known in the art8 An LNA is a nucleic acid incorporating one or more modified RNA or DNA nucleotide residues (in combination with ordinary DNA or RNA residues). In the modified residue an extra covalent bridge connects the 2' and 3' carbons and "locks" the ribose sugar in the 3'-endo structural conformation as normally found in the A-form of RNA and DNA. LNAs include all nucleic acids incorporating locked residues at some or all residue positions. The lock may be achieved by any chemical bridge connecting the 2' and 3' carbons of the sugar moiety. Preferably the lock is achieved in a 2'-O, 4'-C methylene linkage.

LNAs display increased thermal stability, with melting temperature rising by about 5° C. compared to corresponding DNA or RNA oligomers. Because of the elevated melting temperature, the risk of LNA primers and probes forming hairpin structures detrimental to efficient PCR reactions is increased. Good primer and probe design therefore becomes even more essential and in relation to the present application LNA primers and probes corresponding to those disclosed in SEQ ID NOS: 3, 4, 5, 7, 8 and 9 optionally shortened by 1, 2, 3, 4 or 5 residues from either end, are especially preferred.

LNAs can be readily prepared and are commercially available from a number of suppliers.

Minor Groove Binding Moieties

The nucleic acid probes and primers of the invention (including LNA probes and primers) may be conjugated to minor groove binder (MGB) moieties9. MGB moieties are isometrical-shaped groups which bind in the minor groove of a double helix forming between the probe or primer and target. They stabilize the double stranded region and increase the melting temperature and specificity of the probe/primer, allowing shorter probes/primers to be used. Minor groove binding moieties may be readily prepared and attached to primers and probes and are commercially available from a number of suppliers.

Additional Target Sequences

As mentioned above, the methods of the invention for detecting the presence of *N. gonorrhoeae* may further comprise a step of detecting one or more additional target sequence(s). The methods of the invention may further comprise amplifying one or more additional target sequence(s). The methods of the invention may further comprise a step of detecting at least one, at least two, at least three, at least four, at least five, at least six, at least seven, at least eight, at least nine or at least ten additional target sequences. The methods of the invention may further comprise a step of amplifying at least one, at least two, at least three, at least four, at least five, at least six, at least seven, at least eight, at least nine or at least ten additional target sequences.

The techniques described above for detecting and amplifying the first target sequence and/or the second target sequence can also be used for detection and amplification of an internal control nucleic acid sequence. Similarly, the characteristics of primers and probes can be the same as described above.

One or more of the additional target sequence(s) may be further *N. gonorrhoeae* target sequences. One or more of the additional target sequence(s) or may be target sequences from other pathogens. Using one or more additional target sequence(s) from other pathogens allows for simultaneous detection of multiple pathogens.

Detection of Multiple Pathogens

The methods of the invention may be used to detect multiple pathogens simultaneously. For example, the methods may involve detecting *N. gonorrhoeae* and *Chlamydia trachomatis* (*C. trachomatis*). The methods may involve detecting, in addition to *N. gonorrhoeae*, one or both of *C. trachomatis* and *Trichomonas vaginalis* (*T. vaginalis*) in the sample. The methods may also involving detecting other pathogens, particularly pathogens which cause sexually transmitted infections.

The techniques described above for detecting and amplifying the first target sequence and/or the second target sequence can also be used for detection and amplification of target sequences from *C. trachomatis* and *T. vaginalis*. Similarly, the characteristics of primers and probes can be the same as described above.

Where *C. trachomatis* is additionally detected, the method further comprises a step of detecting a *C. trachomatis* specific target sequence. This step may be performed as described in WO 2011/073675. The *C. trachomatis* specific target sequence may comprise at least 10, at least 15, at least 20, at least 25 or at least 30, at least 40, at least 40, at least 50, at least 60, at least 70, at least 80, at least 90 or at least 100 contiguous nucleotides of SEQ ID NO: 15 or a fragment thereof or SEQ ID NO: 16 or a fragment thereof. The step of detecting *C. trachomatis* specific target sequence may comprise a step of hybridising the *C. trachomatis* specific target sequence to a *C. trachomatis* specific nucleic acid probe and identifying the occurrence of hybridisation. Any probe which is capable of hybridising to the *C. trachomatis* specific target sequence may be used. The *C. trachomatis* specific nucleic acid probe may comprise at least 10, at least 12, at least 14, at least 16, at least 18, at least 20, at least 22, at least 24, at least 26, at least 28, at least 30 or at least 32 contiguous nucleotides of SEQ ID NO: 17. The *Chlamydia trachomatis* specific nucleic acid probe may comprise SEQ ID NO: 17. The *Chlamydia trachomatis* specific nucleic acid probe may consist of SEQ ID NO: 17.

The method may further comprise a step of amplifying the *C. trachomatis* specific target sequence. This amplification may be performed using any technique for amplification mentioned above. Preferably PCR is used. The step of amplifying the *C. trachomatis* specific target sequence may involve any primer pair that is capable of amplifying the *C. trachomatis* specific target sequence. Preferably, a forward primer comprising 12 or more contiguous nucleotides selected from SEQ ID NO: 18 wherein the sequence of SEQ ID NO: 18 or its complement may be mutated by up to 5 additions, deletions and/or substitutions of single nucleotides and/or a reverse primer comprising 12 or more contiguous nucleotides selected from SEQ ID NO: 19 wherein the sequence of SEQ ID NO: 19 or its complement may be mutated by up to 5 additions, deletions and/or substitutions of single nucleotides, are used.

Where *T. vaginalis* is additionally detected, the method further comprises a step of detecting a *T. vaginalis* specific target sequence. This step may be performed as described in United Kingdom patent application 1401605.9 (not yet published). The *T. vaginalis* specific target sequence may comprise at least 10, at least 15, at least 20, at least 25 or at least 30, at least 40, at least 40, at least 50, at least 60, at least 70, at least 80, at least 90 or at least 100 contiguous nucleotides of SEQ ID NO: 20 or a fragment thereof or SEQ ID NO: 21 or a fragment thereof. As for the *N. gonorrhoeae* target sequences mentioned above, the *T. vaginalis* specific target sequence may be of any length.

The step of detecting *T. vaginalis* specific target sequence may comprise a step of hybridising the *T. vaginalis* specific target sequence to a *Trichomonas vaginalis* specific nucleic acid probe and identifying the occurrence of hybridisation. Any probe which is capable of hybridising to the *T. vaginalis* specific target sequence may be used. The *T. vaginalis* specific nucleic acid probe may comprise at least 10, at least 12, at least 14, at least 16, at least 18, at least 20 or at least 22 contiguous nucleotides of SEQ ID NO: 22. The *T. vaginalis* specific nucleic acid probe may comprise SEQ ID NO: 22. The *T. vaginalis* specific nucleic acid probe may consist of SEQ ID NO: 22.

The method may further comprise a step of amplifying the *T. vaginalis* specific target sequence. This amplification may be performed using any technique for amplification mentioned above. Preferably PCR is used. The step of amplifying the *T. vaginalis* specific target sequence may involve any primer pair that is capable of amplifying the *T. vaginalis* specific target sequence. Preferably, a forward primer comprising 12 or more contiguous nucleotides selected from SEQ ID NO: 23 wherein the sequence of SEQ ID NO: 23 or its complement may be mutated by up to 5 additions, deletions and/or substitutions of single nucleotides and/or a reverse primer comprising 12 or more contiguous nucleotides selected from SEQ ID NO: 24 wherein the sequence of SEQ ID NO: 24 or its complement may be mutated by up to 5 additions, deletions and/or substitutions of single nucleotides, are used.

As mentioned above, the labels included in the nucleic acid probes used to assist in the detection of nucleic acid sequences from different pathogens are preferably distinguishable from each other. For example, they may be different fluorophores or they may be different electrochemically active agents or electrochemically active labels providing electrochemically distinguishable activity.

Accordingly, the invention also provides methods for detecting *N. gonorrhoeae*, *C. trachomatis* and *T. vaginalis* in a sample. The method may comprise a step of detecting at least one target sequence from *N. gonorrhoeae*, at least one *C. trachomatis* specific target sequence and at least one *T. vaginalis* specific target sequence. Preferably, the at least one target sequence from *N. gonorrhoeae* are selected from NGO1642 or a fragment thereof and NGO1012 or a fragment thereof. Preferably the *C. trachomatis* specific target sequence is SEQ ID NO: 15 or a fragment thereof or SEQ ID NO: 16 or a fragment thereof. Preferably, the *T. vaginalis* specific target sequence is TVAG_003780 (SEQ ID NO: 20) or a fragment thereof or SEQ ID NO: 21 or a fragment thereof.

Compositions

The invention also provides compositions comprising one or more of the primers and/or nucleic acid probes described above.

The compositions of the invention may comprise at least one forward primer and at least one reverse primer capable of hybridising to the first target sequence and/or the second target sequence. The composition may further comprise at least one nucleic acid probe capable of hybridising to the first target sequence and/or the second target sequence. The composition may further comprise a DNA polymerase. These compositions are suitable for performing amplification of the target e.g. by PCR.

The compositions may further comprise an internal control nucleic acid sequence. The compositions may further comprise a forward control primer and a reverse control primer capable of specifically hybridising to the internal control nucleic acid sequence. The composition may further comprise a control nucleic acid probe capable of specifically hybridising to the internal control nucleic acid sequence.

These compositions may be added to a sample and the conditions required for detection and where used amplification applied to the composition in order to detect the presence of *N. gonorrhoeae* in the sample.

The invention also provides kits comprising a composition of the invention. A kit may further comprise instructions for use.

The compositions of the invention may further comprise primers and/or probes useful in the detection of additional target sequences. Such additional target sequences may be from different pathogens such as *C. trachomatis* and/or *T. vaginalis*, as described above.

Cartridge

The invention also provides a cartridge for use in a method of detecting the presence of *N. gonorrhoeae* in a sample. The cartridge allows for rapid point-of-care detection of *N. gonorrhoeae* when used in combination with a suitable detection apparatus (cartridge reader).

The cartridge comprises a sample inlet for receiving a sample, a portion in which a step of amplifying the target can take place, and a portion in which a step of detecting the target sequence(s) can take place.

The cartridge may also comprise a portion in which a step of extracting nucleic acids from the sample can take place. The cartridge may be a pneumatically controlled cartridge.

The cartridge may additionally be used for detecting the presence of additional pathogens such as *C. trachomatis* and/or *T. vaginalis*.

General

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

The term "specifically hybridises" means capable of hybridising to the sequence of the intended target and not to sequences that are not present in the intended target.

Unless specifically stated otherwise, a process comprising a step of mixing two or more components does not require any specific order of mixing. Thus components can be mixed in any order. Where there are three components then two components can be combined with each other, and then the combination may be combined with the third component, etc.

The text above refers in several places to addition, deletion or a substitution of a single nucleotide within a particular sequence. The sequence may be mutated by a number of additions and a number of deletions within the specified sequence. Alternatively, the sequence may be mutated by a number of additions and a number of substitutions within the specified sequence. Alternatively, the sequence may be mutated by a number of substitutions and a number of deletions within the specified sequence. Alternatively, the sequence may be mutated by a number of additions, a number of deletions and a number of substitutions within the specified sequence. In all cases, the number of mutated nucleotides may be 1, 2, 3, 4 or 5.

BRIEF DESCRIPTION OF THE DRAWINGS

FIG. 1. The sequence of NGO1642 (SEQ ID NO: 1), showing the location of hybridisation of two specific primers (SEQ ID NOs: 4 and 5) which amplify the *Neisseria gonorrhoeae* nucleic acid sequence SEQ ID NO: 1, and a specific nucleic acid probe (SEQ ID NO: 3).

FIG. 2. The sequence of a fragment of NGO1642 (SEQ ID NO: 25), showing the location of hybridisation of two specific primers (SEQ ID NOs: 4 and 27) which amplify the *Neisseria gonorrhoeae* nucleic acid sequence SEQ ID NO: 25, and a specific nucleic acid probe (SEQ ID NO: 26).

FIG. 3. The sequence of NGO1012 (SEQ ID NO: 6), showing the location of hybridisation of two specific primers (SEQ ID NOs: 10 and 11) which amplify the *Neisseria gonorrhoeae* nucleic acid sequence SEQ ID NO: 1, and a specific nucleic acid probe (SEQ ID NO: 8).

FIG. 4. Sensitivity of the *N. gonorrhoeae* assay (NGO1642 target sequence) following extraction, nucleic acid amplification and detection using symmetric PCR and a variety of primer pairs.

MODES FOR CARRYING OUT THE INVENTION

Primer Design

Figure 1:
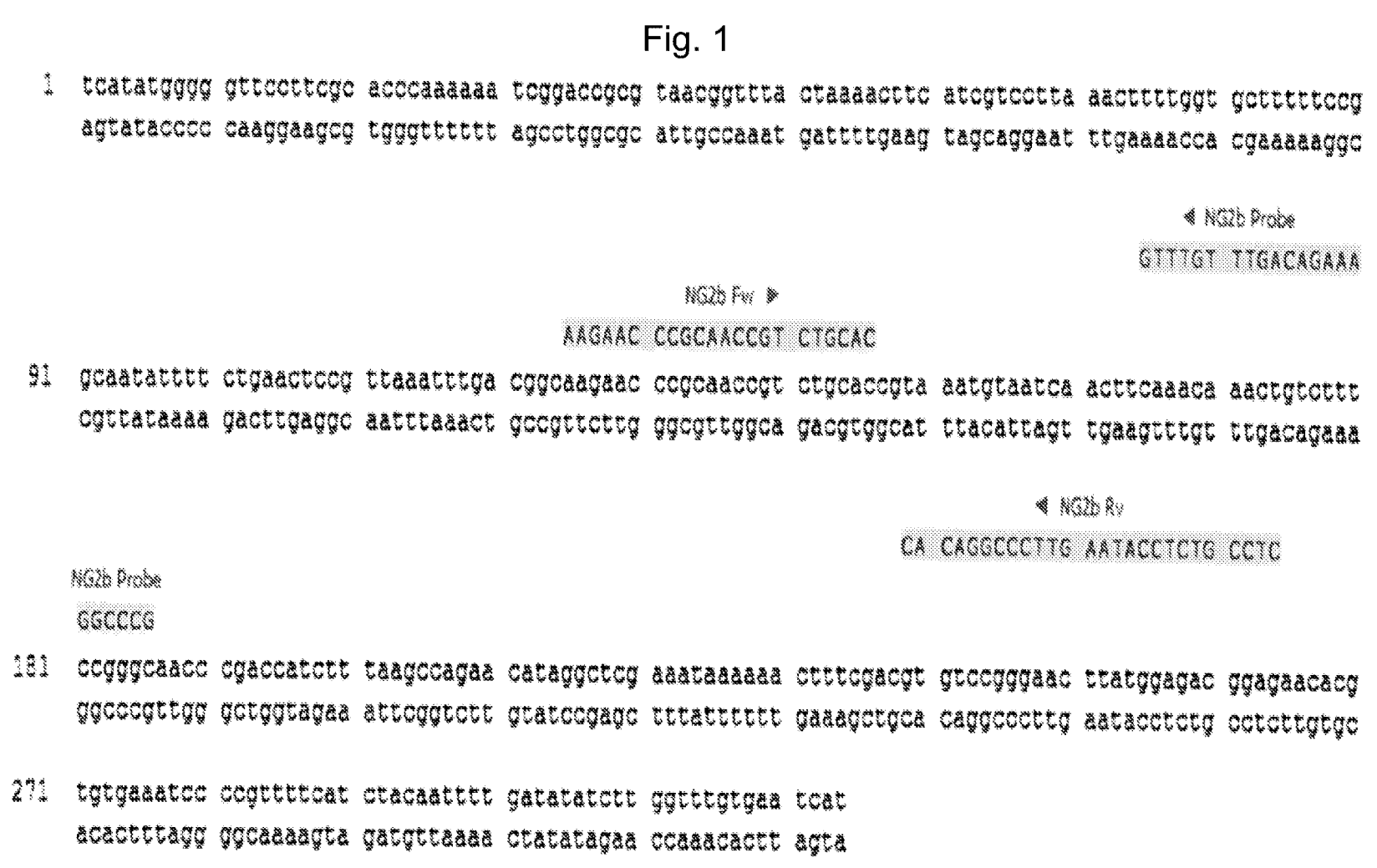
Figure 5:
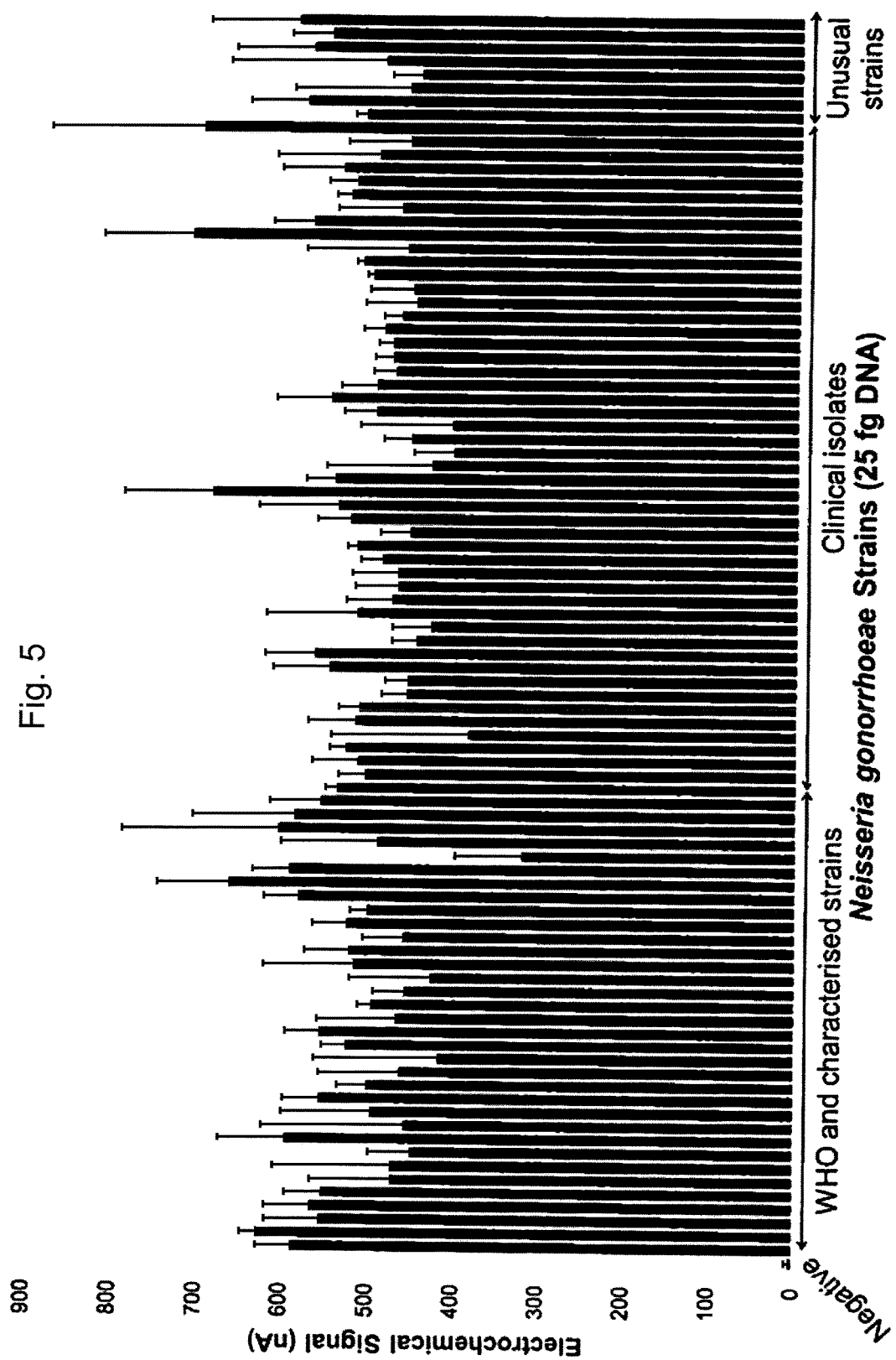
FIG. 5. Inclusivity test of the *N. gonorrhoeae* assay (NGO1642 target sequence) using 92 different *N. gonorrhoeae* isolates and primers having the sequences of SEQ ID NOs: 4 and 5 and a nucleic acid probe having the sequence of SEQ ID NO: 3.

Primer pairs and nucleic acid probes were designed to avoid any variable bases between different strains of *Neisseria gonorrhoeae* and stretches of common bases between other *Neisseria* species. The primers and probes were tested using asymmetric PCR of a known number of genome copies using one of the primer pairs, and subsequent addition of the nucleic acid probe in order to determine the optimum regions for detections (see FIGS. 1-3).

*Neisseria gonorrhoeae* Assay

A sub-circuit assay which mimics a point-of-care cartridge was produced in which three steps take place sequentially: extraction of the *N. gonorrhoeae* nucleic acids from cells, amplifying the target sequence(s) SEQ ID NO: 2 and/or SEQ ID NO: 7 by PCR; and detecting the target sequence by hybridisation of the target sequence to a nucleic acid probe(s) consisting of SEQ ID NO: 3 (which hybridises to SEQ ID NO: 2) and/or SEQ ID NO: 8 (which hybridises to SEQ ID NO: 7), both of which are conjugated to a diferrocene label.

Primers having the nucleic acid sequences of SEQ ID NOs: 4 and 5 were included in the PCR reagents in the sub-circuit assay in order to amplify the sequence of SEQ ID NO: 2 using symmetric PCR. Primers having the nucleic acid sequences of SEQ ID NOs: 10 and 11 were included in the PCR reagents in the cartridge in order to amplify the sequence of SEQ ID NO: 7 using symmetric PCR. Both amplification reactions used were semi-rapid amplification reactions which are completed in less than one hour.

The nucleic acid probes consisting of SEQ ID NOs: 3 and 9 were labelled with ferrocene labels. Following hybridisation of a probe to its target, the double-stranded product was specifically hydrolysed by T7 exonuclease causing the diferrocene label to be cleaved from the rest of the probe. The change in environment of the label which occurs when the label is cleaved from the probe was detected by applying a potential difference to a detection region of the detection sub-circuit and observing changes in the current flowing through the detection region.

The sub-circuit assay also allowed for a step of amplifying a *P. atrosepticum* internal control nucleic acid sequence and a step of detecting the *P. atrosepticum* internal control nucleic acid sequence via hybridisation of the internal control nucleic acid to a control nucleic acid probe and identification of hybridisation. The extraction and amplification of the internal control nucleic acid sequence took place simultaneously with the extraction and amplification of the target sequence(s). Primers having the nucleic acid sequences of SEQ ID NOs: 14 and 15 were included in the PCR reagents in the sub-circuit in order to amplify the internal control nucleic acid sequence of SEQ ID NO: 11, which was also included with the PCR reagents.

A nucleic acid probe having of the nucleic acid sequence of SEQ ID NO: 12 and labelled with a diferrocene label was included in the sub-circuit in order to perform the step of hybridisation of the internal control nucleic acid sequence to a nucleic acid probe. Following hybridisation of the amplification product of the internal control to the control nucleic acid probe, the double-stranded product was specifically hydrolysed and detected in the same way as for the target sequence (see above).

A second sub-circuit assay was produced which is identical to that described above except for that it amplifies SEQ ID NO: 25 rather than SEQ ID NO: 2, includes a reverse primer consisting of SEQ ID NO: 27 rather than SEQ ID NO: 5 and includes a nucleic acid probe consisting of SEQ ID NO: 26 rather than SEQ ID NO: 3.

Determining Assay Sensitivity

The *N. gonorrhoeae* target sequence of SEQ ID NO: 2 (NGO1642) was amplified and detected using the primers and probes mentioned above in samples which contained different copy numbers of the *N. gonorrhoeae* genome in the reaction mixture. The first target sequence (SEQ ID NO: 2) was detected in all samples containing 4,000,000, 400,000, 40,000, 4,000, 400, 40 or 4 genomic copies (see FIG. 4). The first target sequence was not detected in the negative control (see FIG. 4). Therefore the preliminary sensitivity of the *N. gonorrhoeae* assay was found to be 4 genome copies of *N. gonorrhoeae* genomic DNA. The fact that four copies of the first target sequence are present in each genome means that sensitivity is increased because even with a very low genome copy present, a high level of target sequence is present allowing for detection.

This copy number also means that fewer rounds of amplification are required without losing the sensitivity of the test, because even very few rounds of amplification of the target sequence will result in a large amount of amplified target sequence. In order to achieve a point-of-care test it is necessary to use rapid amplification techniques. However, such techniques can lead to false negative results if the sequence is missed because not enough time is taken for adequate hybridisation of primers etc to take place. However, the presence of multiple copies of the target sequence in the genome allows for rapid amplification to be used without the possibility of the target sequence being missed. Furthermore, the fact that a second target sequence has been identified for use in conjunction with the first target sequence means that sensitivity of the assay is increased. Combining a first target sequence which provides an assay with already high sensitivity with a second target sequence, the result is an assay with extremely high sensitivity.

Determining Assay Inclusivity

It is important that the assay is capable of detecting different strains of *N. gonorrhoeae*. There is significant genetic diversity between different strains of *N. gonorrhoeae*. So that the assay was capable of amplifying and detecting the majority, if not all, known strains of *N. gonorrhoeae*, DNA from 92 different strains (including all 35 WHO and characterised control strains, 50 clinical isolates with different NG-MAST types and 7 strains with unusual characteristics including plasmid-less PPNG and TRNG) was isolated and SEQ ID NO: 2 was amplified and detected using PCR at 25 fg DNA/reaction (equivalent to 10 cells) using the NGO1642 primers consisting of SEQ ID NOs: 4 and 5 and a probe consisting of SEQ ID NO: 3. The results of the inclusivity testing are provided in FIG. 5. All strains were detected using the assay. *N. gonorrhoeae* was not detected in the negative control sample. The high level of assay inclusivity reduces the incidence of false negative results.

Figure 6:
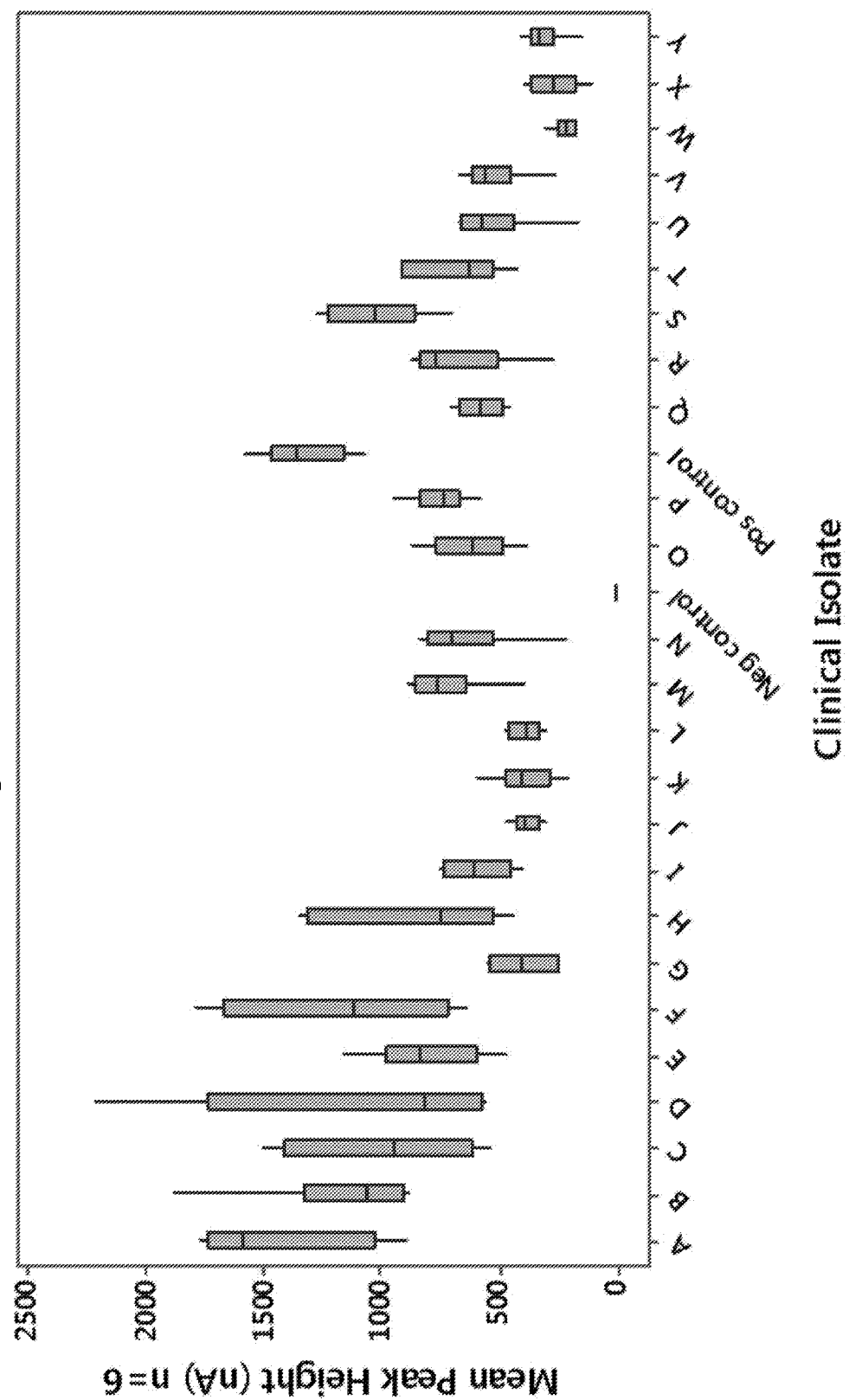
FIG. 6. Further inclusivity test of the *N. gonorrhoeae* assay (NGO1642 target sequence) using 25 different *N. gonorrhoeae* isolates and primers having the sequences of SEQ ID NOs: 4 and 26 and a nucleic acid probe having the sequence of SEQ ID NO: 27.

The inclusivity test described above was also performed using NGO1642 primers consisting of SEQ ID NOs: 4 and 27 and a probe consisting of SEQ ID NO: 26. The results of the inclusivity testing are provided in FIG. 6. All strains were detected using the assay. *N. gonorrhoeae* was not detected in the negative control sample. The high level of assay inclusivity reduces the incidence of false negative results.

Figure 7:
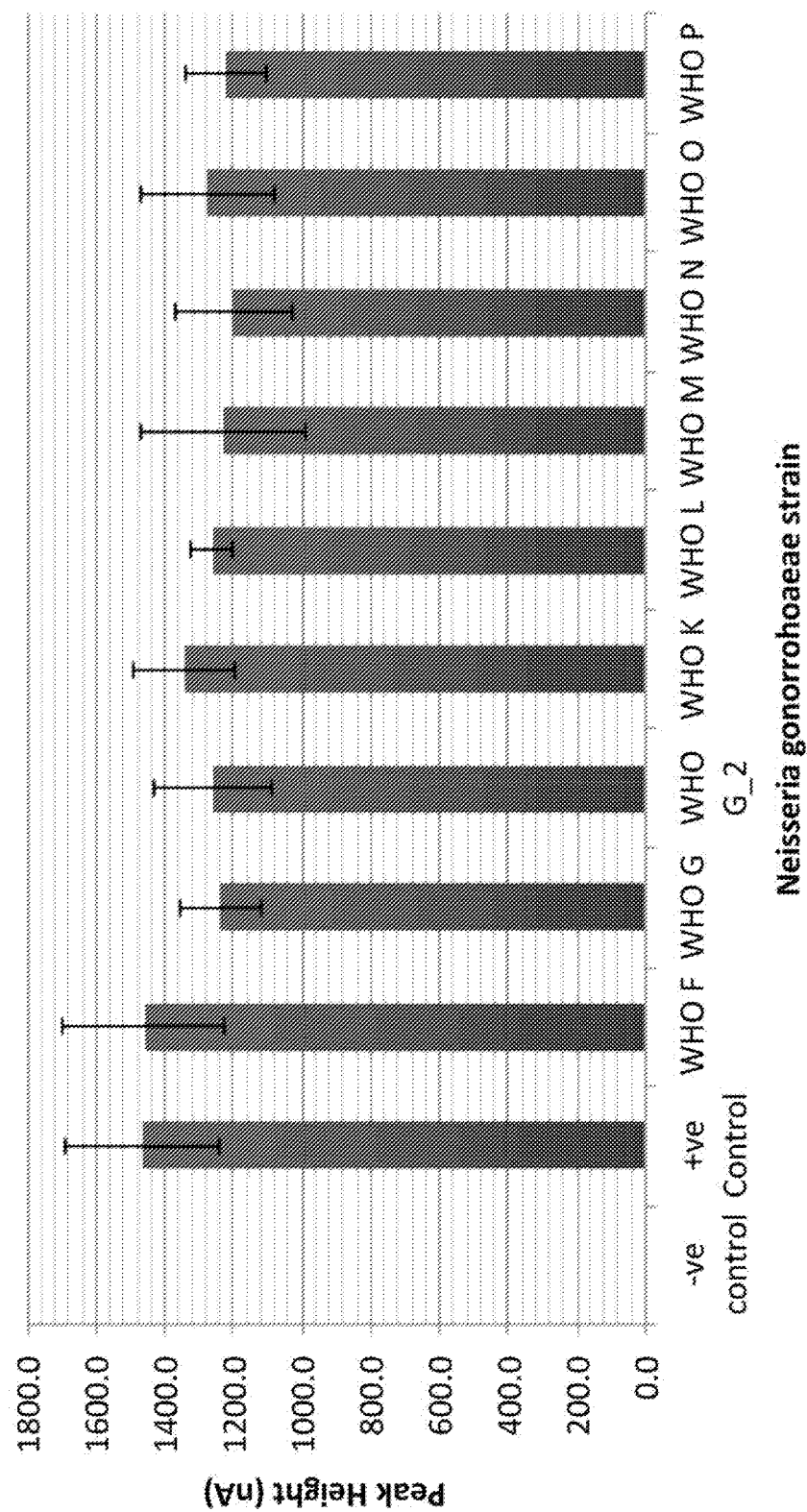
FIG. 7. Initial inclusivity test of the *N. gonorrhoeae* assay (NGO1012 target sequence) using 9 different *N. gonorrhoeae* strains and primers having the sequences of SEQ ID NOs: 9 and 10 and a nucleic acid probe having the sequence of SEQ ID NO: 8.

Initial work relating to the NGO1012 sequence showed that this target sequence is also inclusive. Results using 7 different strains are provided in FIG. 7.

Figure 8:
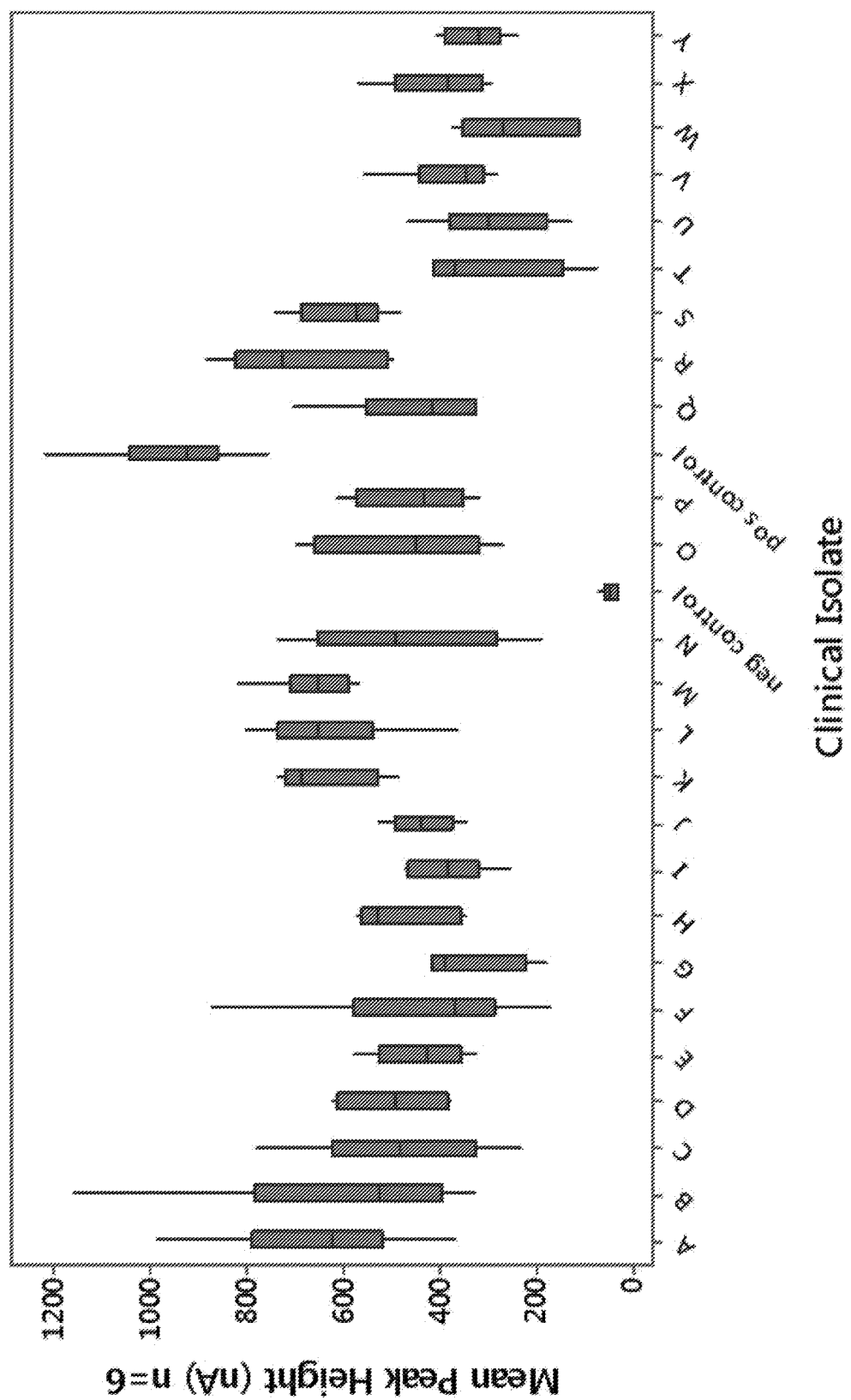
FIG. 8. Further inclusivity test of the *N. gonorrhoeae* assay (NGO1012 target sequence) using 25 different *N. gonorrhoeae* strains and primers having the sequences of SEQ ID NOs: 9 and 10 and a nucleic acid probe having the sequence of SEQ ID NO: 8.

Further inclusivity testing of the NGO1012 sequence was subsequently performed using the NGO1012 primers consisting of SEQ ID NOs: 9 and 10 and a nucleic acid probe consisting of the sequence of SEQ ID NO: 8. The results of the inclusivity testing are provided in FIG. 8. All strains were detected using the assay. *N. gonorrhoeae* was not detected in the negative control sample. The high level of assay inclusivity reduces the incidence of false negative results.

Inclusivity has also been demonstrated by the inventors when the NGO1642 target sequence and the NGO1012 target sequence are tested in triplex with the internal control.

Determining Assay Exclusivity

Figure 9:
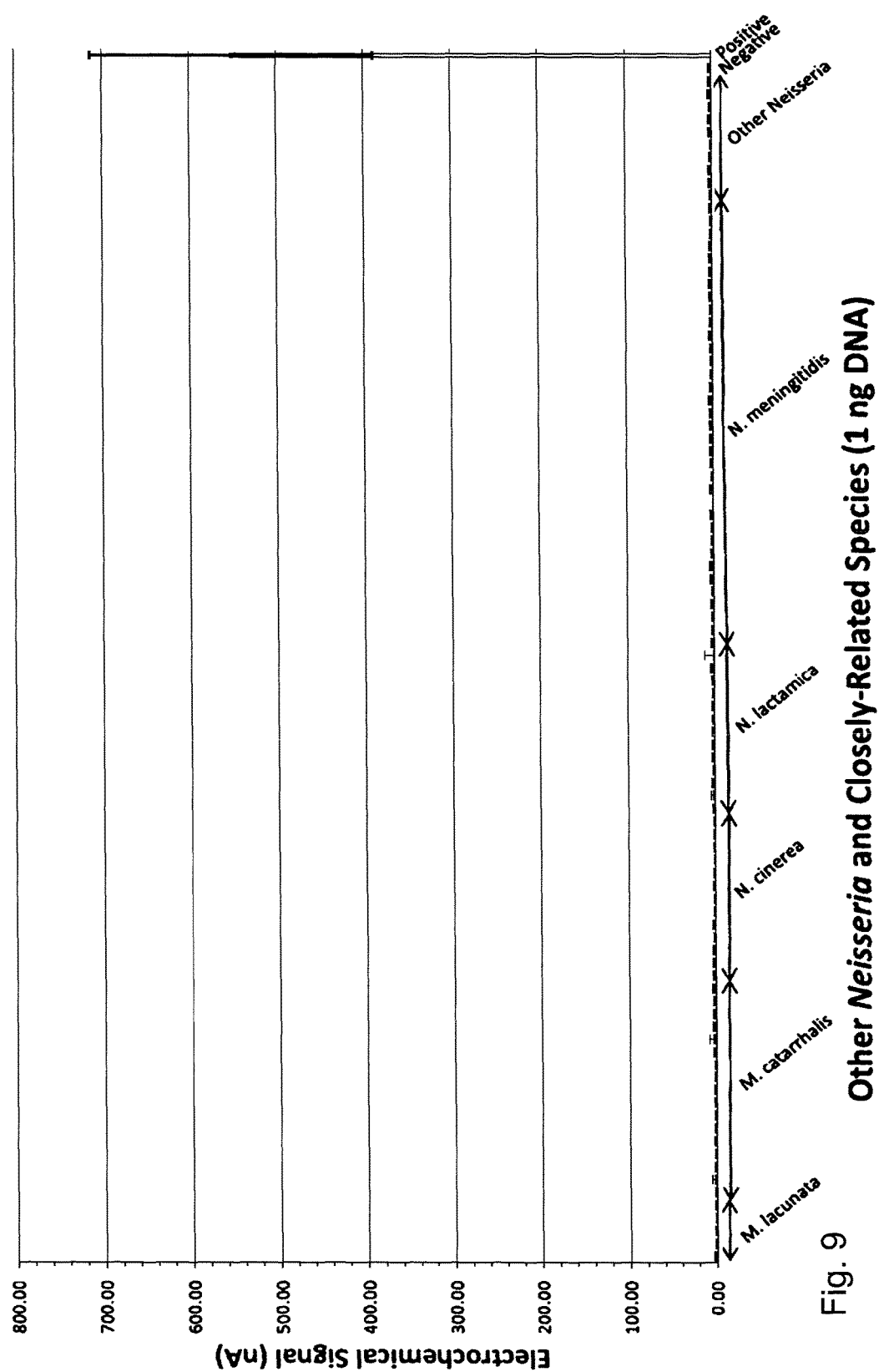
FIG. 9. Exclusivity assay (NGO1642 target sequence) using DNA from a range of Non-gonococcal *Neisseria* species and other closely-related species using primers having the sequences of SEQ ID NOs: 4 and 5 and a nucleic acid probe having the sequence of SEQ ID NO: 3.
Figure 10:
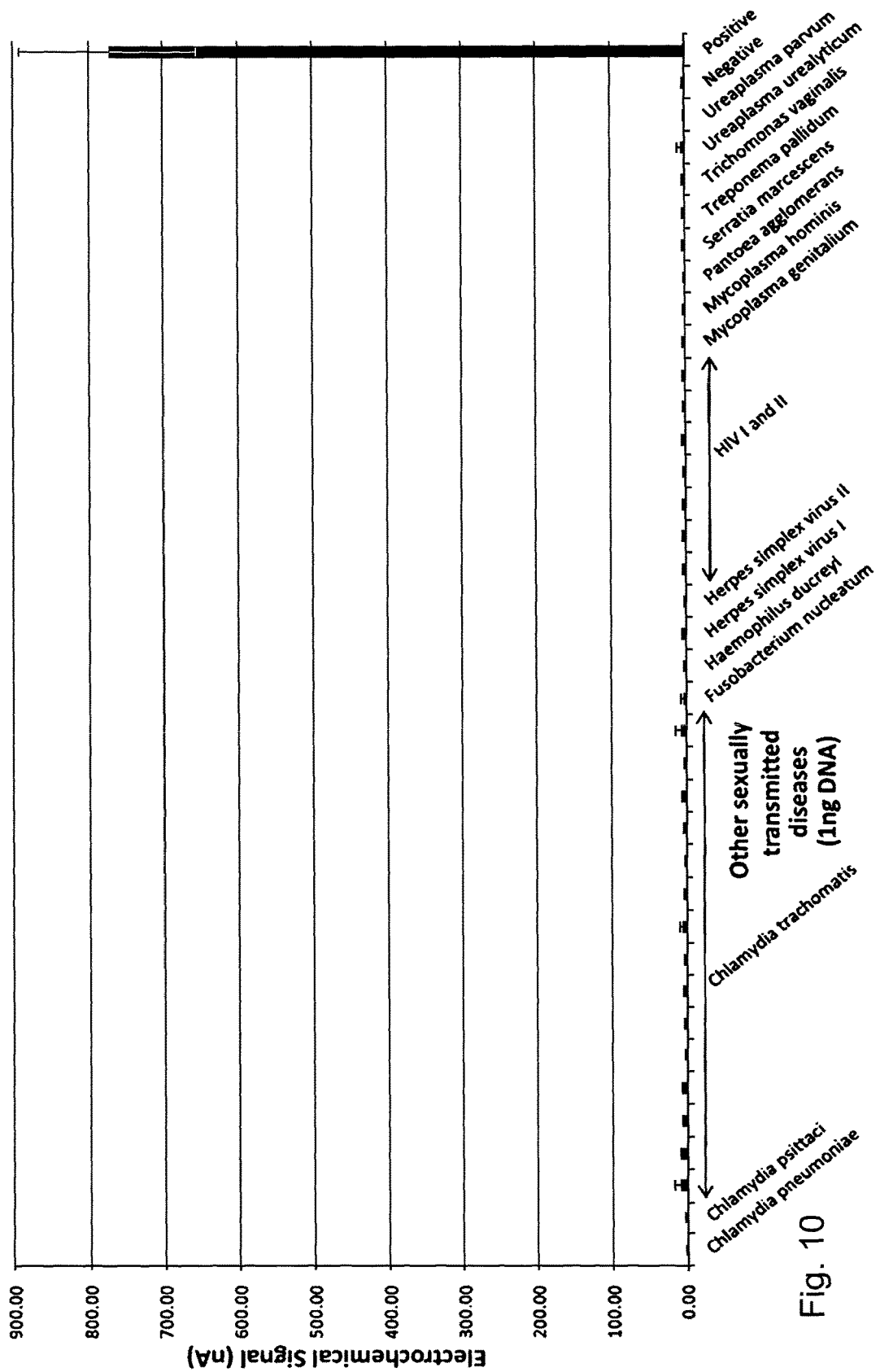
FIG. 10. Exclusivity assay (NGO1642 target sequence) using DNA isolated from a range of bacteria that cause other sexually transmitted infections primers having the sequences of SEQ ID NOs: 4 and 5 and a nucleic acid probe having the sequence of SEQ ID NO: 3.
Figure 11:
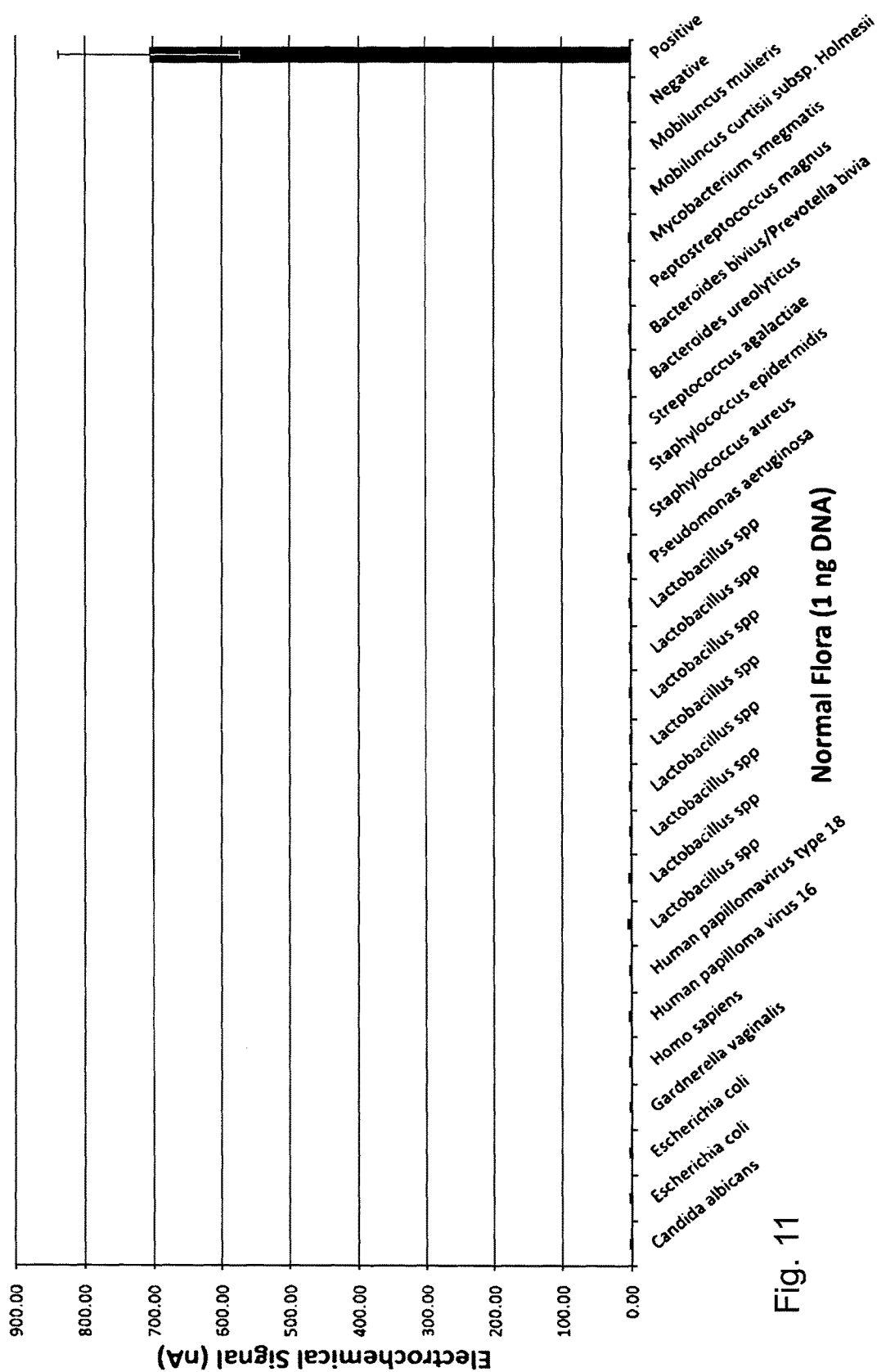
FIG. 11. Exclusivity assay (NGO1642 target sequence) using DNA isolated from bacteria that form part of the normal flora in the genitourinary tract primers having the sequences of SEQ ID NOs: 4 and 5 and a nucleic acid probe having the sequence of SEQ ID NO: 3.
Figure 12:
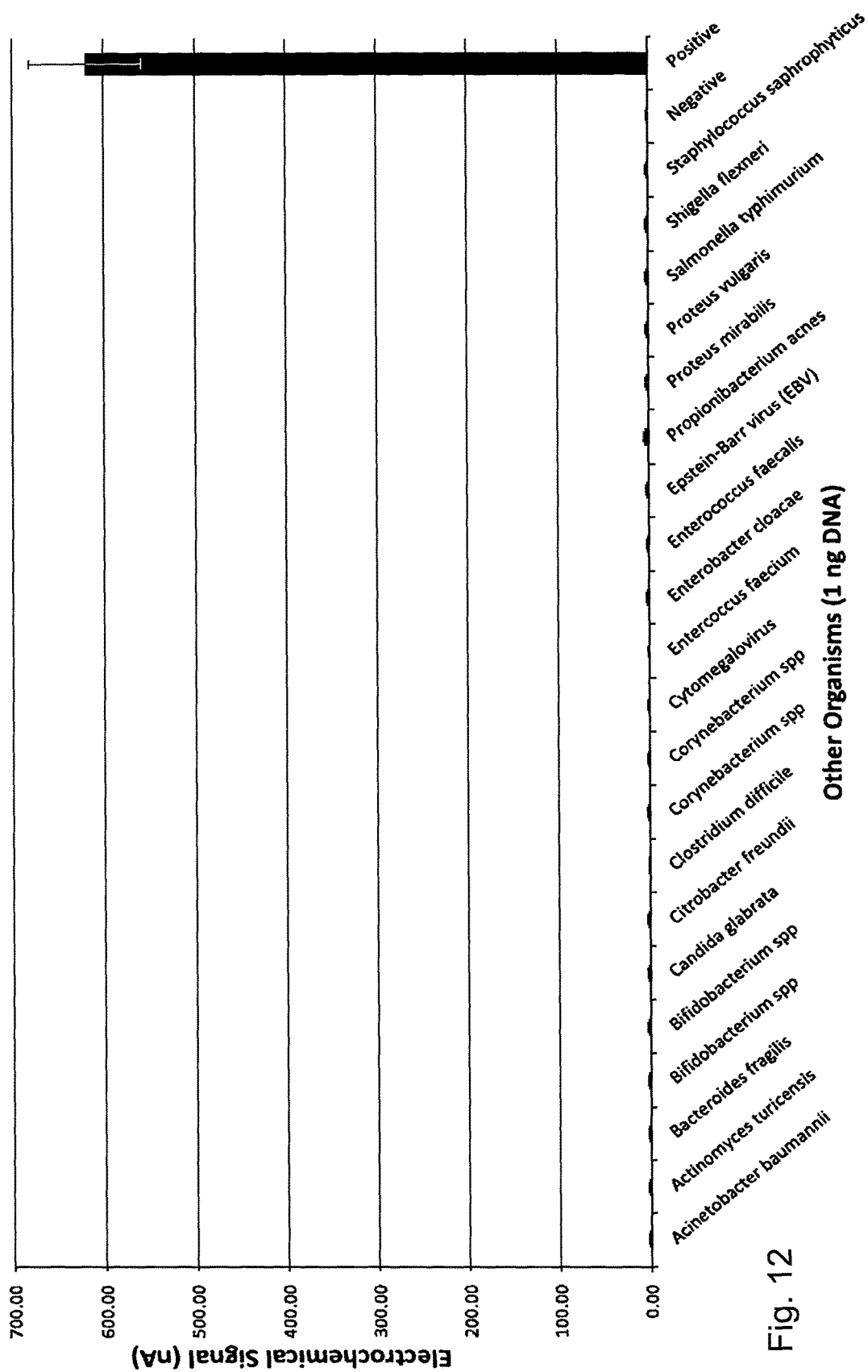
FIG. 12. Exclusivity assay (NGO1642 target sequence) using DNA isolated from bacteria that cause a range of other diseases primers having the sequences of SEQ ID NOs: 4 and 5 and a nucleic acid probe having the sequence of SEQ ID NO: 3.

It is important that the assay is capable of distinguishing the presence of *N. gonorrhoeae* from the presence of other pathogens. Therefore amplification and detection of SEQ ID NO: 2 was performed on samples containing a range of organisms to check exclusivity using primers consisting of the sequences of SEQ ID NOs: 4 and 5 and a nucleic acid probe consisting of the sequence of SEQ ID NO: 3. All samples were analysed in triplicate. Results of the exclusivity testing using non-gonnococcal *Neisseria* species and closely related species are provided in FIG. 9. Results of the exclusivity testing using other organisms that cause sexually transmitted infections (and which are therefore likely to be present at the same sampling sites) such as *C. trachomatis* and HIV I and II are provided in FIG. 10. Results of the exclusivity testing using normal flora commonly found in the genitourinary tract are shown in FIG. 11. Results of the exclusivity testing using other organisms that are on the FDA guidelines cross-reactivity panel for *N. gonorrhoeae* are provided in FIG. 12. No cross-reactivity was demonstrated when the assay was tested against the panel of organisms, i.e. no organism other than *N. gonorrhoeae* was detected at levels higher than those present in the negative control.

Amplification and detection of SEQ ID NO: 25 was also performed on samples containing a range of organisms to check exclusivity using primers consisting of the sequences of SEQ ID NOs: 4 and 27 and a nucleic acid probe consisting of the sequence of SEQ ID NO: 26. All samples were analysed in triplicate. The organisms included in the samples used are provided in Table 1 below.

| Tier 1 | | Tier 2 | |
|---|---|---|---|
| Sample | Organism | Sample | Strain |
| 1 | Moraxella lacunata | 1 | Neisseria cinerea |
| 2 | Moraxella catarrhalis | 2 | Neisseria cinerea |
| 3 | Neisseria cinerea | 3 | Neisseria cinerea |
| 4 | Neisseria elongata | 4 | Neisseria cinerea |
| 5 | Neisseria flava | 6 | Neisseria cinerea |
| 6 | Neisseria flavescens | 8a | Neisseria meningitidis |
| 7 | Neisseria lactamica | 8b | Neisseria meningitidis |
| 8 | Neisseria meningitidis (Serogroup A) | 9 | Neisseria meningitidis |
| 9 | Neisseria meningitidis (Serogroup B) | 10 | Neisseria meningitidis |
| 10 | Neisseria mucosa | 11 | Neisseria meningitidis |
| 11 | Neisseria perflava | 12 | Neisseria meningitidis |
| 12 | Neisseria polysacchareae | 13 | Neisseria meningitidis |
| 13 | Neisseria sicca | 14 | Neisseria lactamica |
| 14 | Neisseria subflava | 16 | Neisseria lactamica |
| 15 | Neisseria denitrificans | 17 | Neisseria lactamica |
| 16 | Neisseria gonorrhoeae | 18 | Neisseria meningitidis |

Figure 13:
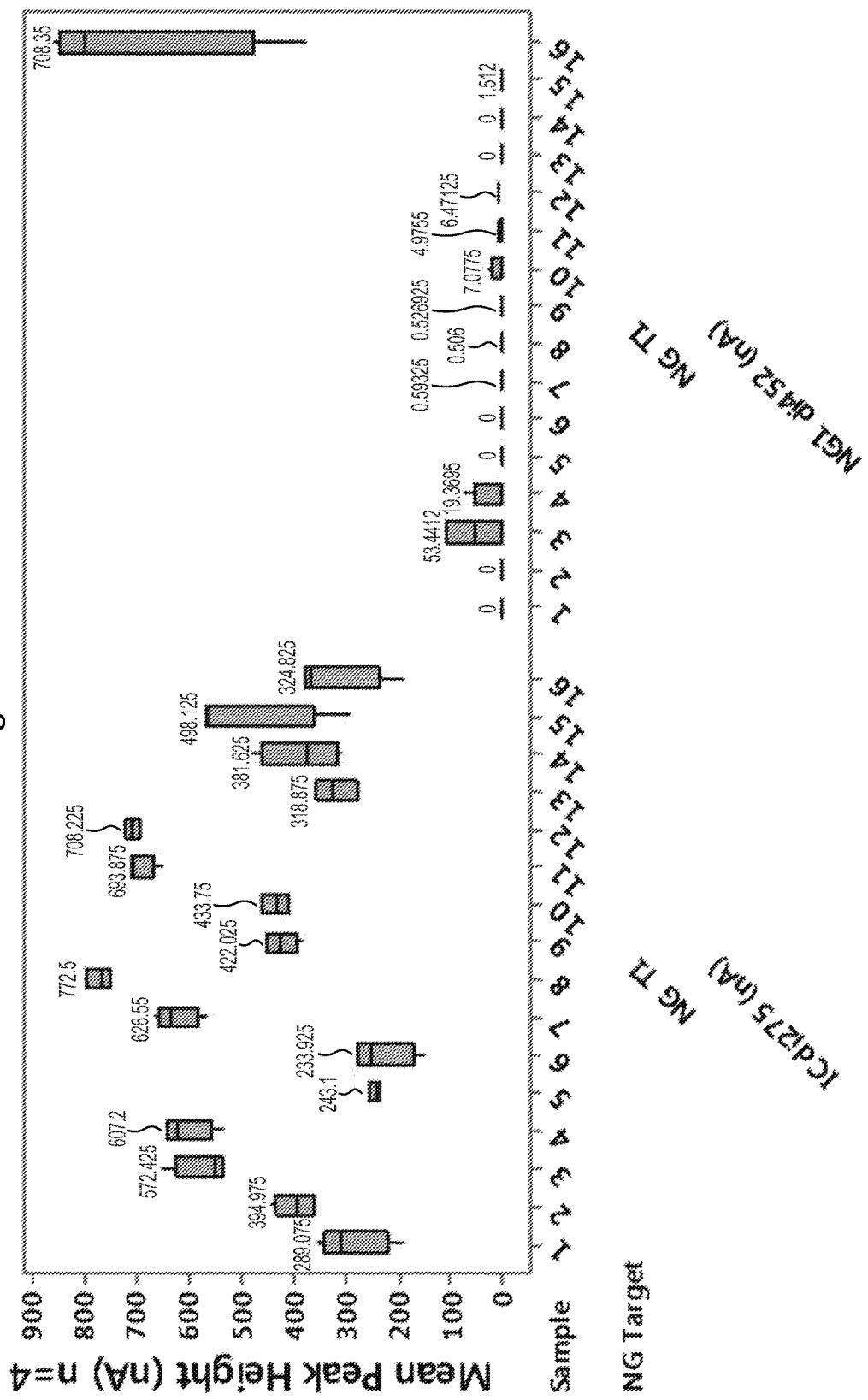
FIG. 13. Exclusivity assay (NGO1642 target sequence) using "Tier 1" DNA isolated from a range of Non-gonococcal *Neisseria* species and other closely-related species using primers having the sequences of SEQ ID NOs: 4 and 26 and a nucleic acid probe having the sequence of SEQ ID NO: 27. The left hand section of the box plot reports the levels of detection of the internal control nucleic acid. The right hand section of the box plot reports the levels of detection of the NGO1642 target sequqence.
Figure 14:
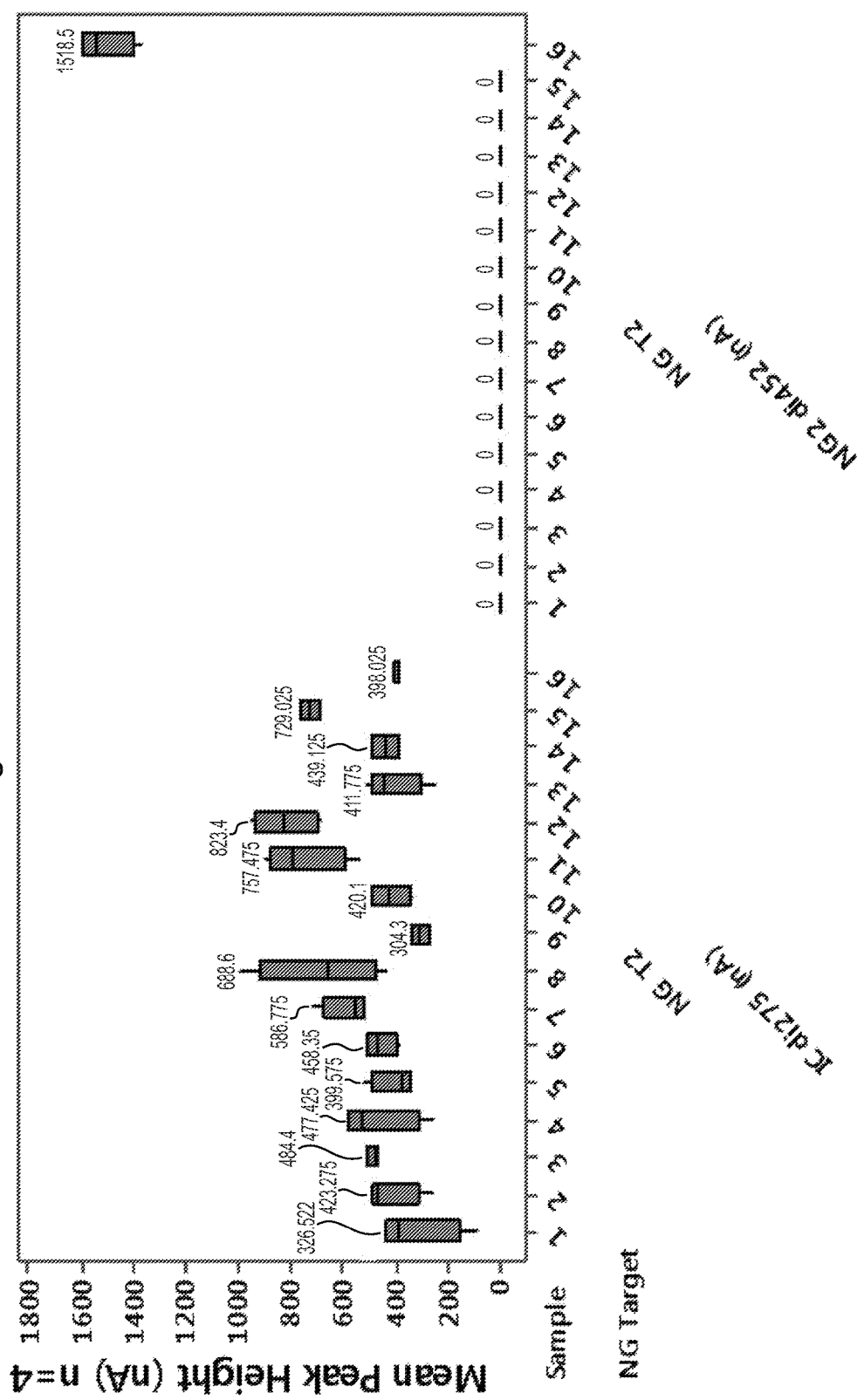
FIG. 14. Exclusivity assay (NGO1642 target sequence) using "Tier 2" DNA isolated from a range of Non-gonococcal *Neisseria* species using primers having the sequences of SEQ ID NOs: 4 and 26 and a nucleic acid probe having the sequence of SEQ ID NO: 27. The left hand section of the box plot reports the levels of detection of the internal control nucleic acid. The right hand section of the box plot reports the levels of detection of the NGO1642 target sequqence.
Figure 15:
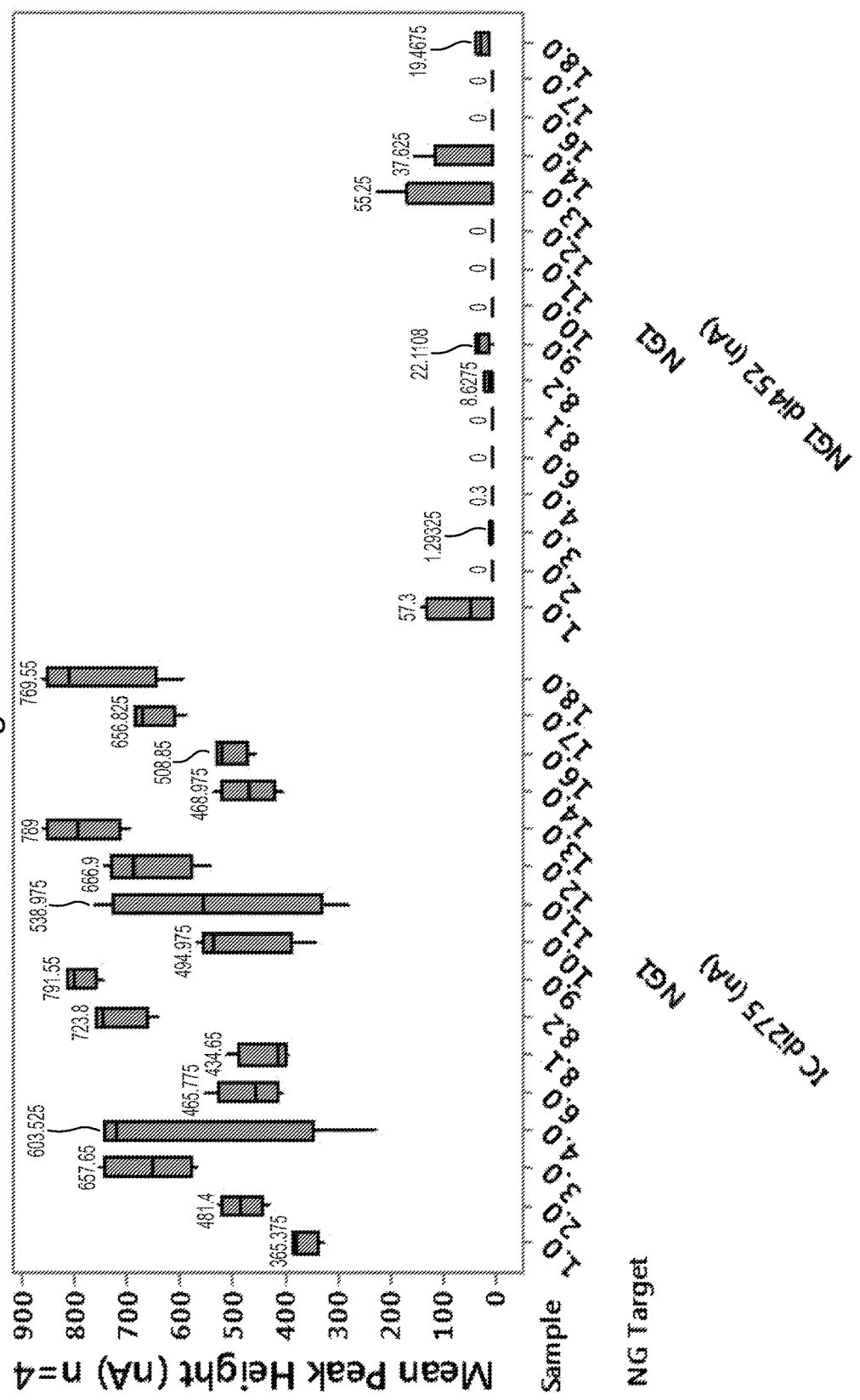
FIG. 15. Exclusivity assay (NGO1012 target sequence) using "Tier 1" DNA isolated from a range of Non-gonococcal *Neisseria* species and other closely-related species using primers having the sequences of SEQ ID NOs: 9 and 10 and a nucleic acid probe having the sequence of SEQ ID NO: 8. The left hand section of the box plot reports the levels of detection of the internal control nucleic acid. The right hand section of the box plot reports the levels of detection of the NGO1012 target sequqence.
Figure 16:
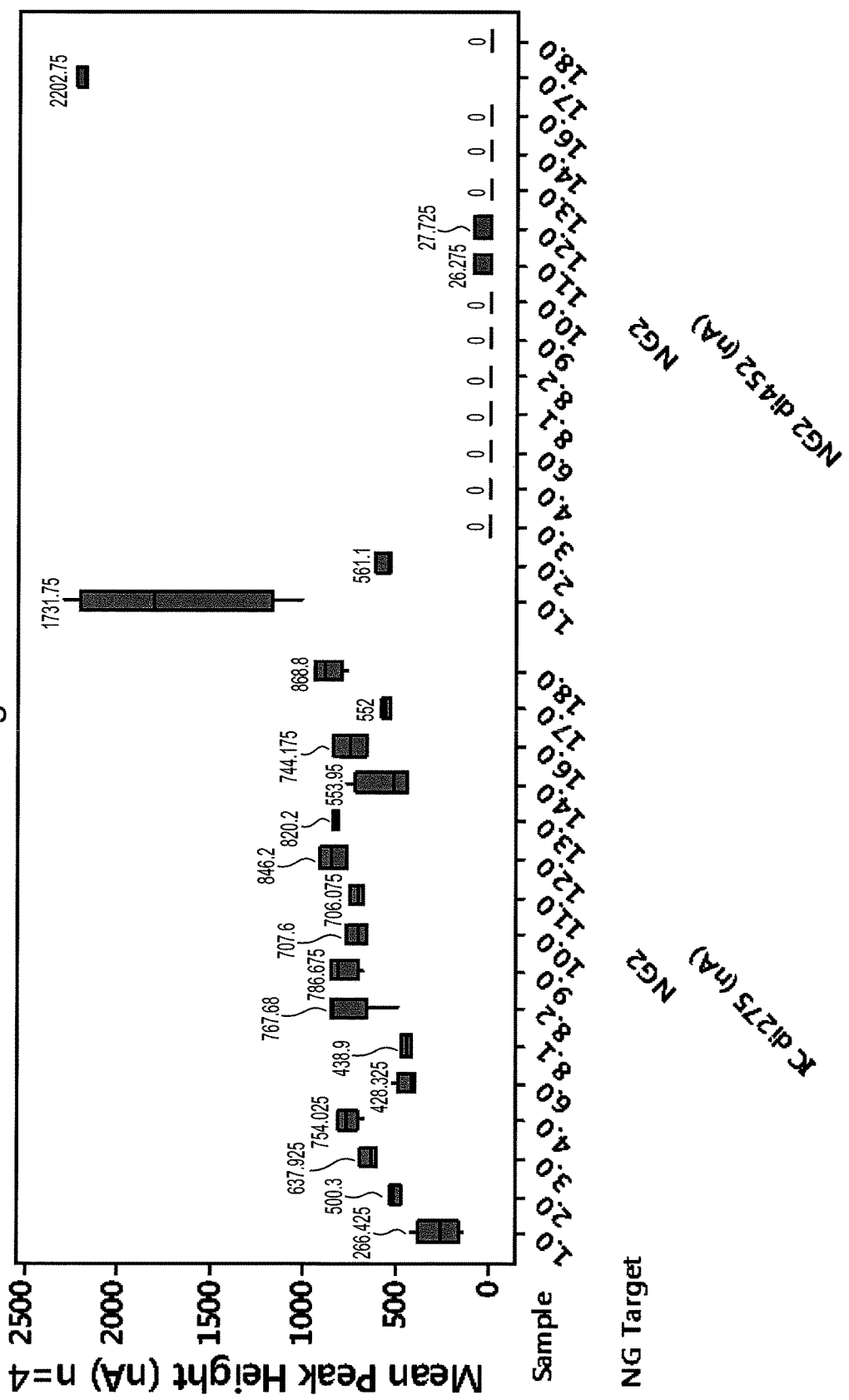
FIG. 16. Exclusivity assay (NGO1012 target sequence) using "Tier 2" DNA isolated from a range of Non-gonococcal *Neisseria* species using primers having the sequences of SEQ ID NOs: 9 and 10 and a nucleic acid probe having the sequence of SEQ ID NO: 8. The left hand section of the box plot reports the levels of detection of the internal control nucleic acid. The right hand section of the box plot reports the levels of detection of the NGO1012 target sequqence.

Results of the exclusivity testing for NGO1642 using "Tier 1" samples are provided in FIG. 13 and results of the exclusivity testing for NGO1642 using "Tier 2" samples are provided in FIG. 14. The NGO1012 target sequence was also found to have good exclusivity. Amplification and detection of SEQ ID NO: 7 was performed on samples containing a range of organisms to check exclusivity using primers consisting of the sequences of SEQ ID NOs: 9 and 10 and a nucleic acid probe consisting of the sequence of SEQ ID NO: 8. All samples were analysed in triplicate. The organisms included in the samples used are provided in Table 1 above. Results of the exclusivity testing using "Tier 1" samples for NGO1012 are provided in FIG. 15 and results of the exclusivity testing using "Tier 2" samples for NGO1012 are provided in FIG. 16.

Although NGO1642 is shown in FIG. 13 to be detected to some level in strains 3 and 4 of the "Tier 1" panel, NGO1012 was not detected at all in any of the samples tested. Therefore, assays in which both NGO1642 and NGO1012 must be detected to provide a positive result would not provide a positive result for these strains.

Again, for the "Tier 2" panel, although NGO1642 was detected in some of the samples and NGO1012 was detected in some of the samples. NGO1642 and NGO1012 were never both detected in a single sample. Therefore, assays in which both NGO1642 and NGO1012 must be detected to provide a positive result would not provide a positive result for these strains.

Testing Assay Compatibility with Internal Control and *C. trachomatis* Assay

In order to optimise a method that could be used to simultaneously detect *N. gonorrhoeae* and other pathogens such as *C. trachomatis* simultaneously, it was confirmed that both the *N. gonorrhoeae* target sequences, the internal control and a *C. trachomatis* specific target sequence could be amplified and detected simultaneously under the same amplification and detection conditions.

Figure 17:
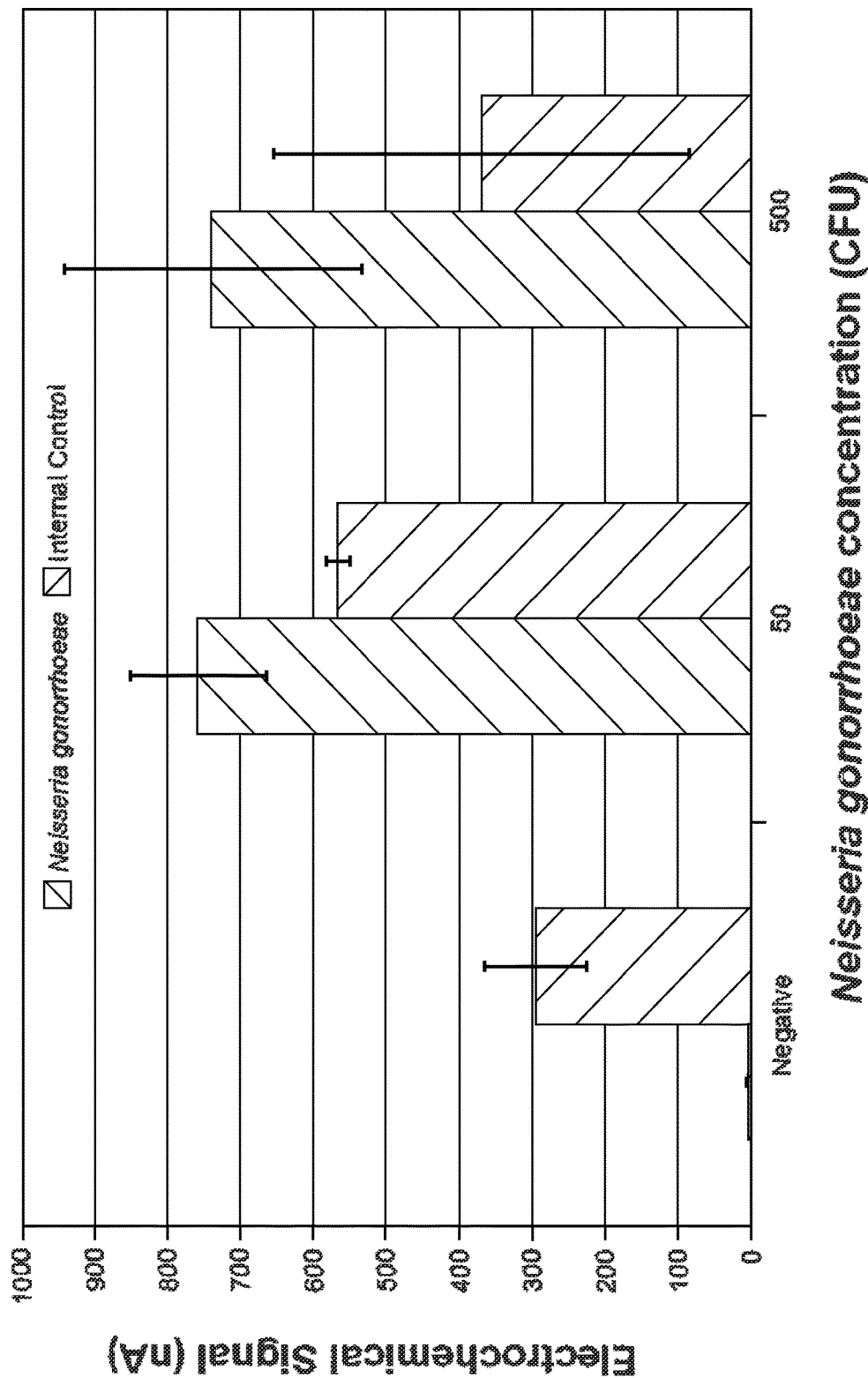
FIG. 17. Detection of the *N. gonorrhoeae* NGO1642 target sequence and the internal control DNA using duplex amplification.

Testing Duplex Assays for a First *N. gonorrhoeae* Target Sequence and Internal Control Firstly, the sub-circuit assay (which closely mimics the assay which is performed on a cartridge) was performed to simultaneously amplify and detect the NGO1642 target sequence of SEQ ID NO: 2 and the internal control sequence. A melting temperature of 94° C., an annealing temperature of 66° C. and an extension temperature of 72° C. were used in the step of amplifying the target sequence. Results of this testing are provided in FIG. 17. FIG. 17 shows that the signal obtained from 50 CFU is easily distinguishable from that of a negative sample. It also shows that an internal control sequence known to be compatible with a method of detecting *C. trachomatis* (as demonstrated in WO 2011/073675) is also compatible with a method of detecting *N. gonorrhoeae*.

Figure 18:
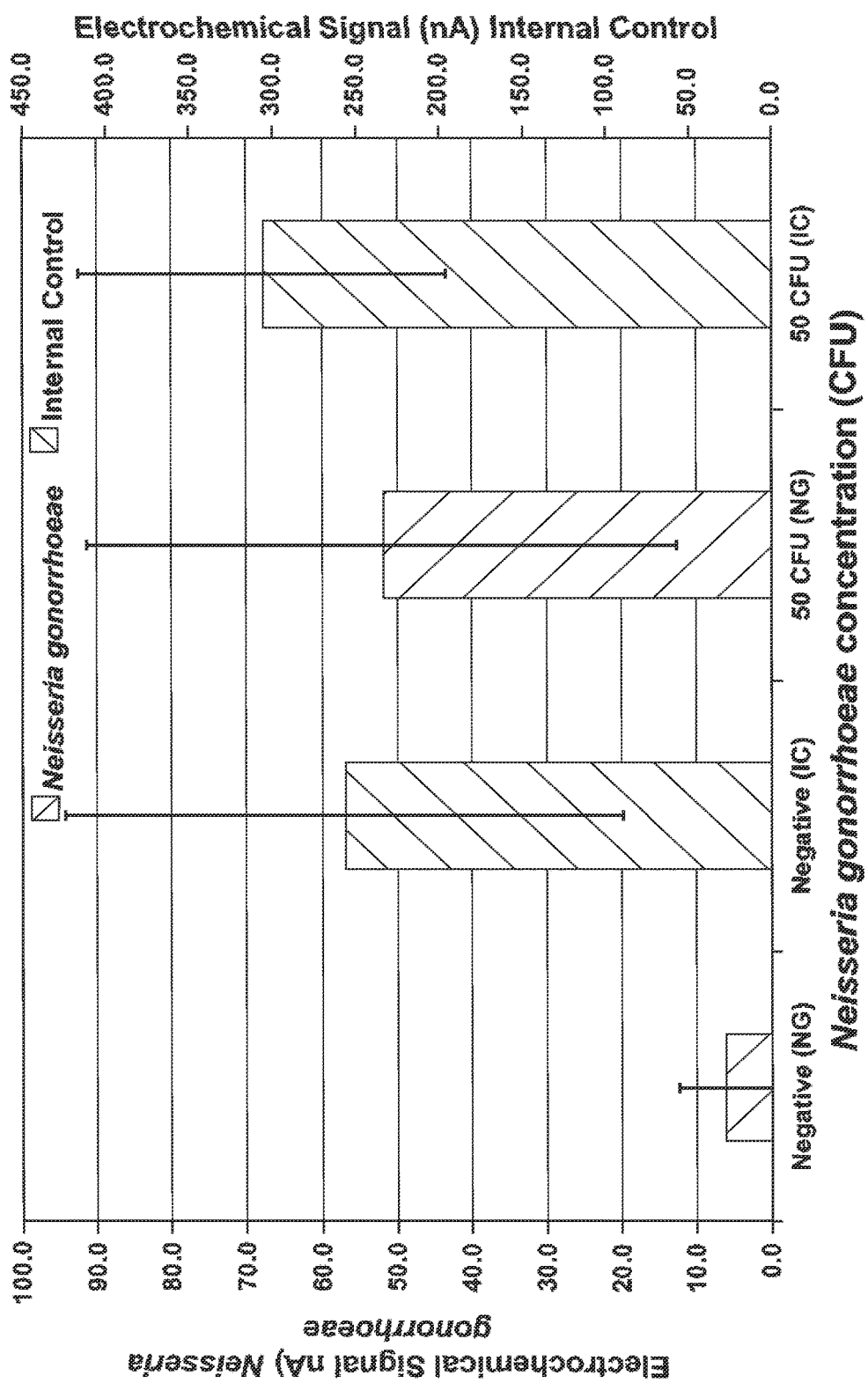
FIG. 18. Sensitivity of the *N. gonorrhoeae* assay when the *Neisseria gonorrhoeae* NGO1642 target sequence and the internal control DNA are amplified and detected in parallel.

Eighteen discrete replicates using 50 CFUs were performed with an equivalent number of negative replicates. The PCR was performed using a "semi-rapid" cycling programme using a 95° C. melting temperature and a 65° C. annealing temperature. This two-step PCR method has been shown to be useful in amplifying *C. trachomatis* specific target sequences. Results of this testing are provided in FIG. 18. FIG. 18 shows that there is a clear differentiation between the electrochemical signals for a 50 CFU sample and a negative sample, and also shows that the internal control nucleic acid sequence can be reliably amplified in a duplex assay with *N. gonorrhoeae* using "semi-rapid" PCR.

Testing Samples with a *N. gonorrhoeae* Target Sequence and a *C. trachomatis* Target Sequence Samples were tested to ensure that extraction of a target sequence present at a low concentration was not inhibited by the presence of a target sequence at a high concentration and that PCR was not affected by the relative DNA concentrations in the sample.

A negative (no target), low (100 CFU/IFU), medium (1,000 CFU/IFU) and high concentration (100,000 CFU/IFU) of each target was tested with a constant high level (100,000 CFU/IFU) of the other organism present.

Figure 19:
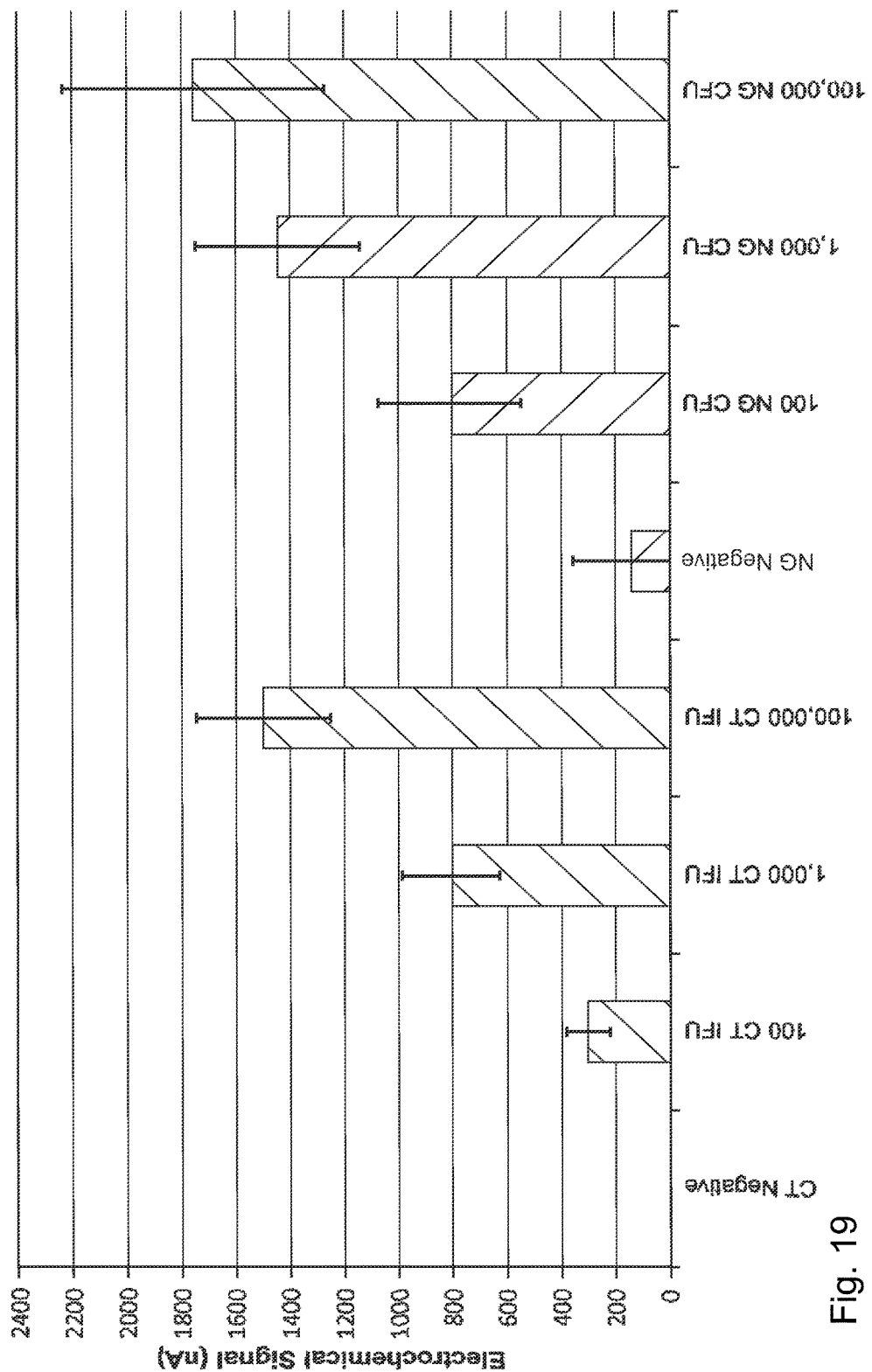
FIG. 19. Sensitivity of the *N. gonorrhoeae* assay (NGO1642 target sequence) in the presence of a high concentration of a *C. trachomatis* target sequence and the *C. trachomatis* assay in the presence of a high concentration of a *N. gonorrhoeae* target sequence.

The required concentration of each organism was dosed on to a swab and then the swab suspended in transport buffer. Three replicate samples using three separate swabs were used for each test condition. Internal control DNA was added prior to the sample extraction. This was extracted and amplified simultaneously, with the PCR performed as a duplex. This was used to verify the test had worked, where the internal control failed these results were omitted. No internal control failures were observed. The results of this testing are provided in FIG. 19. FIG. 19 confirms that the presence of one organism at a high concentration does not affect the extraction of DNA from another organism present at a lower concentration.

Testing Assay Performance in Clinical Samples 123 samples were obtained for testing. The samples were a mix of swab and urine samples and had been pre-typed, as 100 negative samples and 23 positive samples.

The *N. gonorrhoeae* NGO1642 (SEQ ID NO: 2) subcircuit assay was performed on each sample. The internal control DNA was added to the sample prior to extraction. The internal control DNA was extracted and amplified simultaneously with the NGO1642 target sequence as a duplex. The internal control was used to verify that the test had worked, and where internal control failed the results were omitted.

Figure 20:
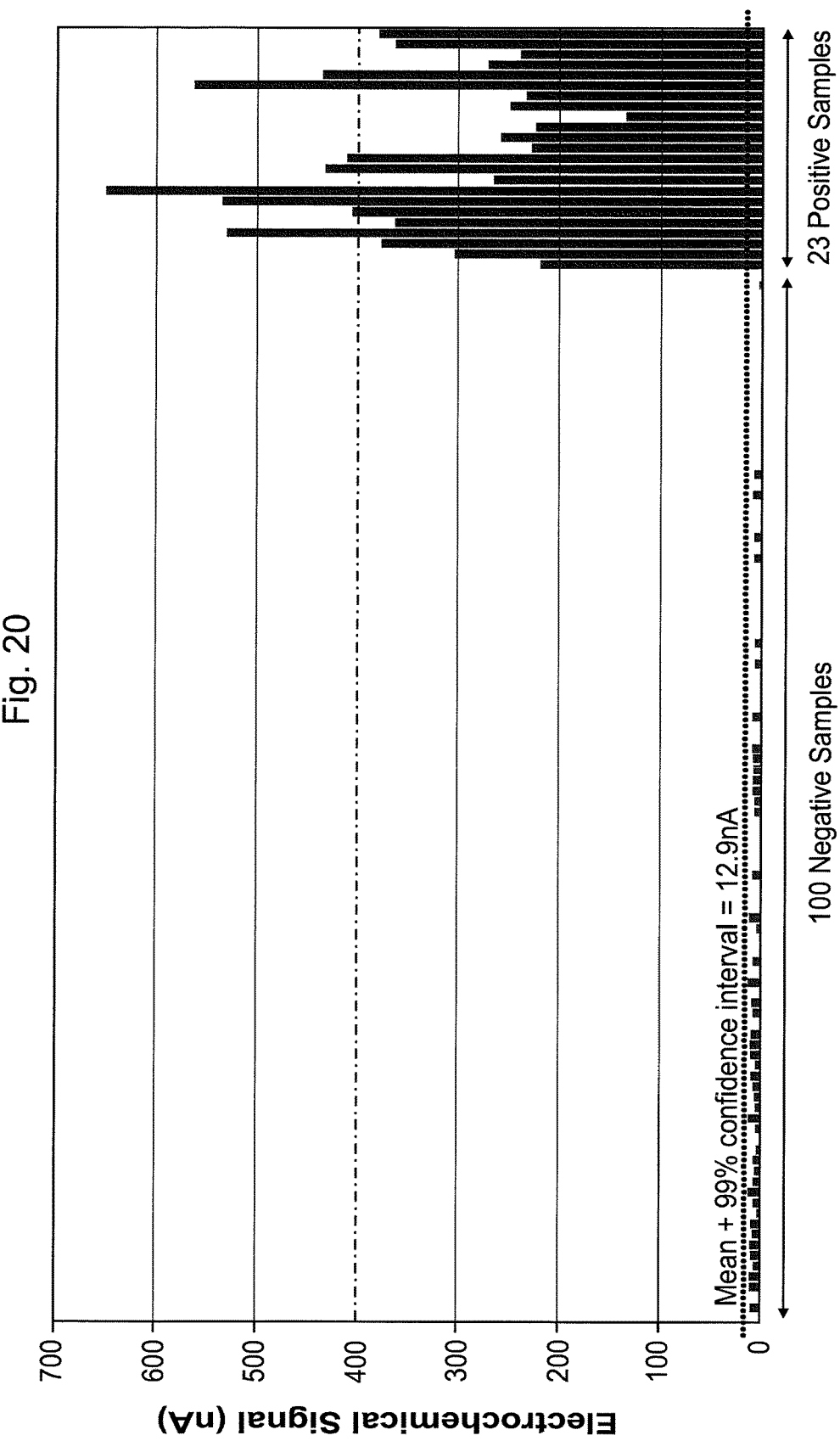
FIG. 20. Frequency distribution of clinical samples tested using the *Neisseria gonorrhoeae* assay (NGO1642 target sequence) to determine assay sensitivity and specificity.

A preliminary assay "cut-off" was assigned based on the negative mean plus 2.58× standard deviation of the mean (a 99% confidence interval). All results for the positive samples are significantly higher than the imposed cut-off value, showing there is clear differentiation between the negative and positive samples tested. Using these criteria the assay shows 100% clinical sensitivity and 100% clinical specificity. Only one sample result was omitted due to a failure of the internal control to be amplified and detected. These results are provided in FIG. 20.

Testing a Triplex Assay for Detecting Two *N. gonorrhoeae* Targets

Tests were performed to confirm that a triplex assay in which both the NGO1642 target sequence (SEQ ID NO: 2) and the NGO1012 target sequence (SEQ ID NO: 7) could be detected down to 25 fg, or 10 copies, of each sequence. It was also confirmed that the *P. atrosepticum* internal control DNA could be simultaneously be amplified in triplex with the *N. gonorrhoeae* target sequences.

Figure 21:
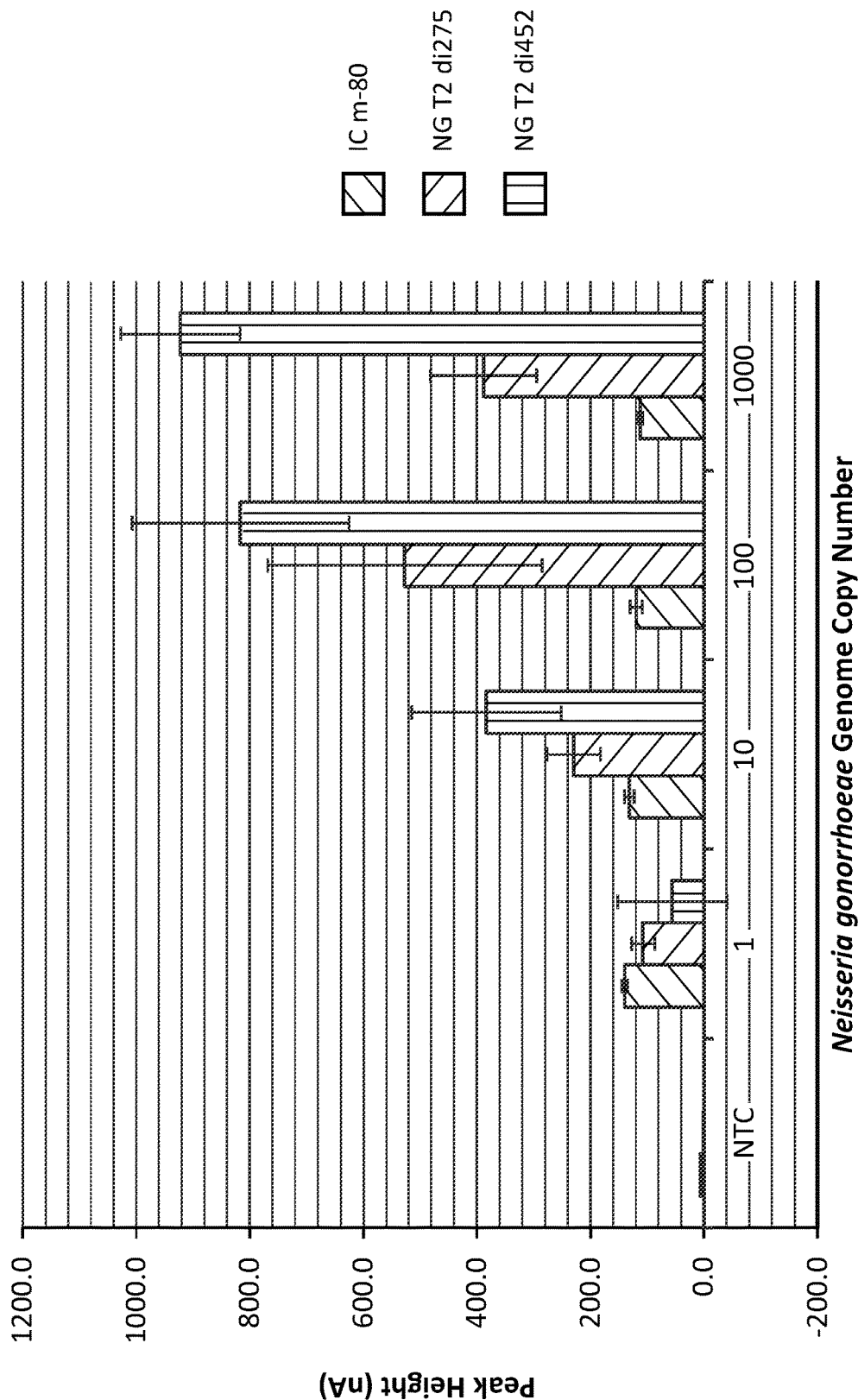
FIG. 21. Sensitivity of the *Neisseria gonorrhoeae* assay using both NGO1642 and NGO1012 target sequences with the internal control DNA amplified and detected in parallel with the two target sequences.

A baseline thermocycling program was used to amplify the target sequences involving a melting temperature of 94° C. for 5 seconds, an annealing temperature of 65° C. for 30 seconds and an extension temperature of 75° C. for 30 seconds. A DNA mix of *N. gonorrhoeae* DNA and internal control DNA were amplified and detected in triplex together. The results of this testing are provided in FIG. 21. FIG. 21 shows that *N. gonorrhoeae* can be detected using the triplex assay down to a very low genome copy number.

REFERENCES

1. Wiedmann M. et al. PCR Methods and Applications 1994 3(4)S51-64
2. Walker et al. Nucleic Acids Res.1992. 20(7) 1691-1696
3. Wroblewski J. et al. J. Clin. Microbiol. 2006:44(9): 3306-3312
4. Compton J. Nature 1991:350(6313):91-2
5. Vincent M. et al. EMBO Rep. 2004 5(8) 795-800
6. Notomi et al. Res. 2000 23 (12):E63.
7. Pearce et al. (2011) *IEEE Trans Biomed Eng.* 58(3): 755-758.
8 Devor (2005) Integrated DNA technologies technical bulletin
9 Katyavin et al. (2000) Nucleic Acid Res. 28(2):655-661

The invention claimed is:

1. A method of detecting the presence of *Neisseria gonorrhoeae* in a sample comprising:
   amplifying a first target sequence comprising SEQ ID NO: 1 and a second target sequence comprising SEQ ID NO: 6;
   hybridising the first target sequence to a nucleic acid probe comprising SEQ ID NO: 3 and a ferrocene label;
   hybridising the second target sequence to a nucleic acid probe comprising SEQ ID NO: 8 and a ferrocene label; and
   identifying the occurrence of hybridisation by detecting the state of the labelled probes, wherein said step of amplifying the first target sequence and the second target sequence uses the polymerase chain reaction and involves the use of forward primers consisting of SEQ ID NOs: 4 and 9 and reverse primers consisting of SEQ ID NOs: 5 and 10.

* * * * *

SEQUENCE LISTING

<160> NUMBER OF SEQ ID NOS: 27

<210> SEQ ID NO 1
<211> LENGTH: 324
<212> TYPE: DNA
<213> ORGANISM: Neisseria Gonorrhoeae

<400> SEQUENCE: 1

```
tcatatgggg gttccttcgc acccaaaaaa tcggaccgcg taacggttta ctaaaacttc      60
atcgtcctta aacttttggt gcttttccg gcaatatttt ctgaactccg ttaaatttga     120
cggcaagaac ccgcaaccgt ctgcaccgta aatgtaatca acttcaaaca aactgtcttt     180
ccgggcaacc cgaccatctt taagccagaa cataggctcg aaataaaaaa ctttcgacgt     240
```

```
gtccgggaac ttatggagac ggagaacacg tgtgaaatcc ccgttttcat ctacaatttt      300
gatatatctt ggtttgtgaa tcat                                             324

<210> SEQ ID NO 2
<211> LENGTH: 140
<212> TYPE: DNA
<213> ORGANISM: Neisseria Gonorrhoeae

<400> SEQUENCE: 2
aagaacccgc aaccgtctgc accgtaaatg taatcaactt caaacaaact gtctttccgg       60
gcaacccgac catctttaag ccagaacata ggctcgaaat aaaaaacttt cgacgtgtcc      120
gggaacttat ggagacggag                                                  140

<210> SEQ ID NO 3
<211> LENGTH: 22
<212> TYPE: DNA
<213> ORGANISM: Artificial Sequence
<220> FEATURE:
<223> OTHER INFORMATION: Probe

<400> SEQUENCE: 3
gcccggaaag acagtttgtt tg                                                22

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
aagaacccgc aaccgtctgc ac                                                22

<210> SEQ ID NO 5
<211> LENGTH: 26
<212> TYPE: DNA
<213> ORGANISM: Artificial Sequence
<220> FEATURE:
<223> OTHER INFORMATION: Primer

<400> SEQUENCE: 5
ctccgtctcc ataagttccc ggacac                                            26

<210> SEQ ID NO 6
<211> LENGTH: 879
<212> TYPE: DNA
<213> ORGANISM: Neisseria Gonorrhoeae

<400> SEQUENCE: 6
atgtctgttg tcaatacggc tgaaaatagt ttttttcaga tagcggcagc catacaactc       60
aaagaggaag cagagtttat tgaggattcc gcacaatttg cccacatgtt gaccgatgca      120
caactgaata caaatgcacc gggtggtatt ttgttggttt taaaaggtag ggttggagat      180
accggtaagc cgttttttatg tgtaattaag gctgaacctc aagatgggtt ccgaaccaaa     240
gaagaggatg actttatcac gattgaattc ttagaagaat tattactgac cgattcagca      300
agattattca agataggttt tttggtggct gaaacagtaa ggccgctaga gcaaatacaa      360
tctgggaatt atcgagcttt tttgtatgac catctgatga cacaaacgga aactagaccg      420
gcagcttcct atttctatca agtattcttg ggtatgagta tagctgcttc ttcccgtaaa      480
ttgacgcagg attttttttga gtggacacgc aattttatcg ataactctga tttaagtgat      540
```

```
gatgcaaaat tagatgcgca tgaagcattg cgcgttacat tgaaaagtgc ggaagcaacc    600
attagtgtaa ataattttgc ccaaaatcat ttacctcaag aaaaacgaac agcttataca    660
gaatttatgg tggaaaagga ttttcctcaa aatgccgtaa gtaaagatat tgaatatatt    720
aaaactcgtt tacgcaaacg gaggtcttac ggatttagta acggtgtagt tatcttgact    780
cctcccgagc atactcagga ctatatggaa attgcgccaa cggaagatgg ggaatatact    840
gttgtcctaa ttaaaggaca gttacaacaa caaaaatga                           879

<210> SEQ ID NO 7
<211> LENGTH: 91
<212> TYPE: DNA
<213> ORGANISM: Neisseria Gonorrhoeae

<400> SEQUENCE: 7
acgcaaacgg aggtcttacg gatttagtaa cggtgtagtt atcttgactc ctcccgagca    60
tactcaggac tatatggaaa ttgcgccaac g                                   91

<210> SEQ ID NO 8
<211> LENGTH: 29
<212> TYPE: DNA
<213> ORGANISM: Artificial Sequence
<220> FEATURE:
<223> OTHER INFORMATION: Probe

<400> SEQUENCE: 8
cggtgtagtt atcttgactc ctcccgagc                                      29

<210> SEQ ID NO 9
<211> LENGTH: 27
<212> TYPE: DNA
<213> ORGANISM: Artificial Sequence
<220> FEATURE:
<223> OTHER INFORMATION: Primer

<400> SEQUENCE: 9
acgcaaacgg aggtcttacg gatttag                                        27

<210> SEQ ID NO 10
<211> LENGTH: 27
<212> TYPE: DNA
<213> ORGANISM: Artificial Sequence
<220> FEATURE:
<223> OTHER INFORMATION: Primer

<400> SEQUENCE: 10
cgttggcgca atttccatat agtcctg                                        27

<210> SEQ ID NO 11
<211> LENGTH: 387
<212> TYPE: DNA
<213> ORGANISM: Pectobacterium Atrosepticium

<400> SEQUENCE: 11
ctaccgtgta gggtcatagg cattgacctc atggctccac ggaatcgtgc gatcgtcaac    60
tgcgacgtgc cattcacagt gcgtaagagc accgcgaatc tcggataaac actggcacca   120
gtgctgtacg ccaatccaga ttgcttcttc ctcgctgtcg ggaagtttgg ttgaaccgga   180
gagcacgatc cctttcctaa agacgttacc gattttcaca ttgagggcga atcaaagga   240 ttcccagttc aggcctgtac ccgtcgtcag atatttctca atttggtcat taacagaatg   300
```

```
gcgttggacg atctccttca cggcagatat ctctttctgg ctcagggatt ttttacgtcg    360
agcggtgtaa tagagcgaaa ttgccac                                        387
```

<210> SEQ ID NO 12
<211> LENGTH: 33
<212> TYPE: DNA
<213> ORGANISM: Artificial Sequence
<220> FEATURE:
<223> OTHER INFORMATION: Probe

<400> SEQUENCE: 12

```
ggagagcacg atccctttcc taaagacgtt acc                                 33
```

<210> SEQ ID NO 13
<211> LENGTH: 18
<212> TYPE: DNA
<213> ORGANISM: Artificial Sequence
<220> FEATURE:
<223> OTHER INFORMATION: Primer

<400> SEQUENCE: 13

```
tgtcgggaag tttggttg                                                  18
```

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14

```
cctgaactgg gaatcctttg                                                20
```

<210> SEQ ID NO 15
<211> LENGTH: 252
<212> TYPE: DNA
<213> ORGANISM: Chlamydia Trachomatis

<400> SEQUENCE: 15

```
atgaattcaa atatagaata taggcaatat cgtatagata tactgagctg ttttatctgc    60
ttgctaatga tggtttggac actagtcagc atcaagctag gagattctct aggaggcatc   120
attcctggat gcttaggata cttactggct aaaaggaagc atcgccgtcc tgtccgctgg   180
ttcttcctta cttttttctt tggcattgcc tctggaatct ccttgtcgt tcttcatcct    240 aagcaaaagt aa                                                       252
```

<210> SEQ ID NO 16
<211> LENGTH: 148
<212> TYPE: DNA
<213> ORGANISM: Chlamydia Trachomatis

<400> SEQUENCE: 16

```
gtttggacac tagtcagcat caagctagga gattctctag gaggcatcat tcctggatgc    60
ttaggatact tactggctaa aaggaagcat cgccgtcctg tccgctggtt cttccttact   120
tttttctttg gcattgcctc tggaatct                                      148
```

<210> SEQ ID NO 17
<211> LENGTH: 23
<212> TYPE: DNA
<213> ORGANISM: Artificial Sequence
<220> FEATURE:
<223> OTHER INFORMATION: Probe

```
<400> SEQUENCE: 17
ctgtccgctg gttcttcctt act                                              23

<210> SEQ ID NO 18
<211> LENGTH: 29
<212> TYPE: DNA
<213> ORGANISM: Artificial Sequence
<220> FEATURE:
<223> OTHER INFORMATION: Primer

<400> SEQUENCE: 18
gtttggacac tagtcagcat caagctagg                                        29

<210> SEQ ID NO 19
<211> LENGTH: 26
<212> TYPE: DNA
<213> ORGANISM: Artificial Sequence
<220> FEATURE:
<223> OTHER INFORMATION: Primer

<400> SEQUENCE: 19
agattccaga ggcaatgcca aagaaa                                           26

<210> SEQ ID NO 20
<211> LENGTH: 933
<212> TYPE: DNA
<213> ORGANISM: Trichomonas Vaginalis

<400> SEQUENCE: 20
atgtcttcat ctacgtcatg tattaaatgc ttcattttat ctccattaaa aatgcaagtc      60
agaaatattc agaacatagc accgagtcta actgacaaga gtataaagat atactatgaa     120
cacgttatga tgaaacctac caaaattcaa gaaagtcagt atacttatga atatccaagg     180
cactgggtag agtatgtagg aggtgagaaa gctattgaaa tcagacaggt tcgaagtatt     240
ccagcaagaa gaacaatatt attgaagaac tttaatgttt tgaggtataa tgatgaaaca     300
aagaagcaag atagttttcc tgttgctgtg tatgtgaacc tagacacagg agatgacatg     360
aaagttttta acacaaagct tcaaacggta gtgagagaac aactgactgc ggaaggacat     420
ccattacctt cagaagttag catagcatat aattttgaaa caaactcaat agattttaaa     480
gtcatctctg caaagaagtc aggttttaca tttaatgaag cagatgtata ttcgaatgaa     540
aacttcaaag ctattgcatg gttagataat gacgattgct ttaagaaaat atttaaattc     600
agtgactcaa agatgtcaat agatgaccct cgtggaatgt taccatcgac gtttacagtt     660
gaaggttcag caggattgct tacaagattg tcaattggtg gtatttggtc tcgtgagaac     720
attgttataa aatccagtat aagtgaattt gctgaagaat ctatattatg tctttcaaac     780
tacatgtatt cgccaccgaa gcattatagt ataacaaact tgtcagtaa gtttaacata     840 agacttgtcg aaccttcttc aatgaaagat gttgtgctac ctaaagatgg aaaggatgga     900
ctcattattg agatgatttt aatagcatat taa                                  933

<210> SEQ ID NO 21
<211> LENGTH: 137
<212> TYPE: DNA
<213> ORGANISM: Trichomonas Vaginalis

<400> SEQUENCE: 21
aacacaaagc ttcaaacggt agtgagagaa caactgactg cggaaggaca tccattacct      60
```

-continued tcagaagtta gcatagcata taattttgaa acaaactcaa tagattttaa agtcatctct    120
gcaaagaagt caggttt    137

<210> SEQ ID NO 22
<211> LENGTH: 23
<212> TYPE: DNA
<213> ORGANISM: Artificial Sequence
<220> FEATURE:
<223> OTHER INFORMATION: Probe

<400> SEQUENCE: 22
gactgcggaa ggacatccat tac    23

<210> SEQ ID NO 23
<211> LENGTH: 28
<212> TYPE: DNA
<213> ORGANISM: Artificial Sequence
<220> FEATURE:
<223> OTHER INFORMATION: Primer

<400> SEQUENCE: 23
aacacaaagc ttcaaacggt agtgagag    28

<210> SEQ ID NO 24
<211> LENGTH: 26
<212> TYPE: DNA
<213> ORGANISM: Artificial Sequence
<220> FEATURE:
<223> OTHER INFORMATION: Primer

<400> SEQUENCE: 24
aaacctgact tctttgcaga gatgac    26

<210> SEQ ID NO 25
<211> LENGTH: 128
<212> TYPE: DNA
<213> ORGANISM: Neisseria Gonorrhoeae

<400> SEQUENCE: 25
aagaacccgc aaccgtctgc accgtaaatg taatcaactt caaacaaact gtctttccgg    60
gcaacccgac catctttaag ccagaacata ggctcgaaat aaaaaacttt cgacgtgtcc    120
gggaactt    128

<210> SEQ ID NO 26
<211> LENGTH: 29
<212> TYPE: DNA
<213> ORGANISM: Artificial Sequence
<220> FEATURE:
<223> OTHER INFORMATION: Probe

<400> SEQUENCE: 26
aacaaactgt ctttccgggc aacccgacc    29

<210> SEQ ID NO 27
<211> LENGTH: 22
<212> TYPE: DNA
<213> ORGANISM: Artificial Sequence
<220> FEATURE:
<223> OTHER INFORMATION: Primer

<400> SEQUENCE: 27
aagttcccgg acacgtcgaa ag    22